United States Patent [19]
Weir et al.

[11] Patent Number: 5,831,937
[45] Date of Patent: Nov. 3, 1998

[54] PORTABLE RANGING SYSTEM FOR ANALYZING GAIT

[75] Inventors: Richard F. ff. Weir, Chicago; Dudley S. Childress, Wilmette, both of Ill.; Joseph N. Licameli, Camillus, N.Y.

[73] Assignee: Northwestern University, Evanston, Ill.

[21] Appl. No.: 833,601

[22] Filed: Apr. 9, 1997

[51] Int. Cl.⁶ .................................................. G01S 15/58
[52] U.S. Cl. ............................................................ 367/128
[58] Field of Search ........................ 367/128, 98; 600/407

[56] References Cited

U.S. PATENT DOCUMENTS

| | | | |
|---|---|---|---|
| 4,315,325 | 2/1982 | Blades | 367/98 |
| 4,939,701 | 7/1990 | Brunner et al. | 367/128 |

*Primary Examiner*—Daniel T. Pihulic
*Attorney, Agent, or Firm*—McAndrews, Held, & Malloy, Ltd.

[57] ABSTRACT

A portable ranging system for analyzing gait is disclosed comprising a transponder having an infrared receiver and an ultrasound emitter, a base unit having an infrared emitter and an ultrasound receiver, and a computer terminal. During gait analysis, the transponder is worn by a subject at approximately the level of the body center of mass. As the subject walks away from the base unit, the base unit continuously causes, at a constant sampling rate, the ultrasound emitter to emit ultrasound pulses. These ultrasound pulses are received by the ultrasound receiver of the base unit. The computer terminal, by counting during the flight of each ultrasound pulse, is able to calculate the time of flight of each ultrasound pulse, and thus calculate and display in real time the forward progression of the subject. At the end of the walking trial, the computer terminal displays the instantaneous velocity profile, or gait velocigram (GVG), for that trial. From the GVG, the computer terminal calculates and displays gait parameters such as gait speed, cadence, step time, step length, peak-to-peak variation, and time to achieve steady state walking. From the displayed data, gait pathologies can be readily identified.

84 Claims, 23 Drawing Sheets

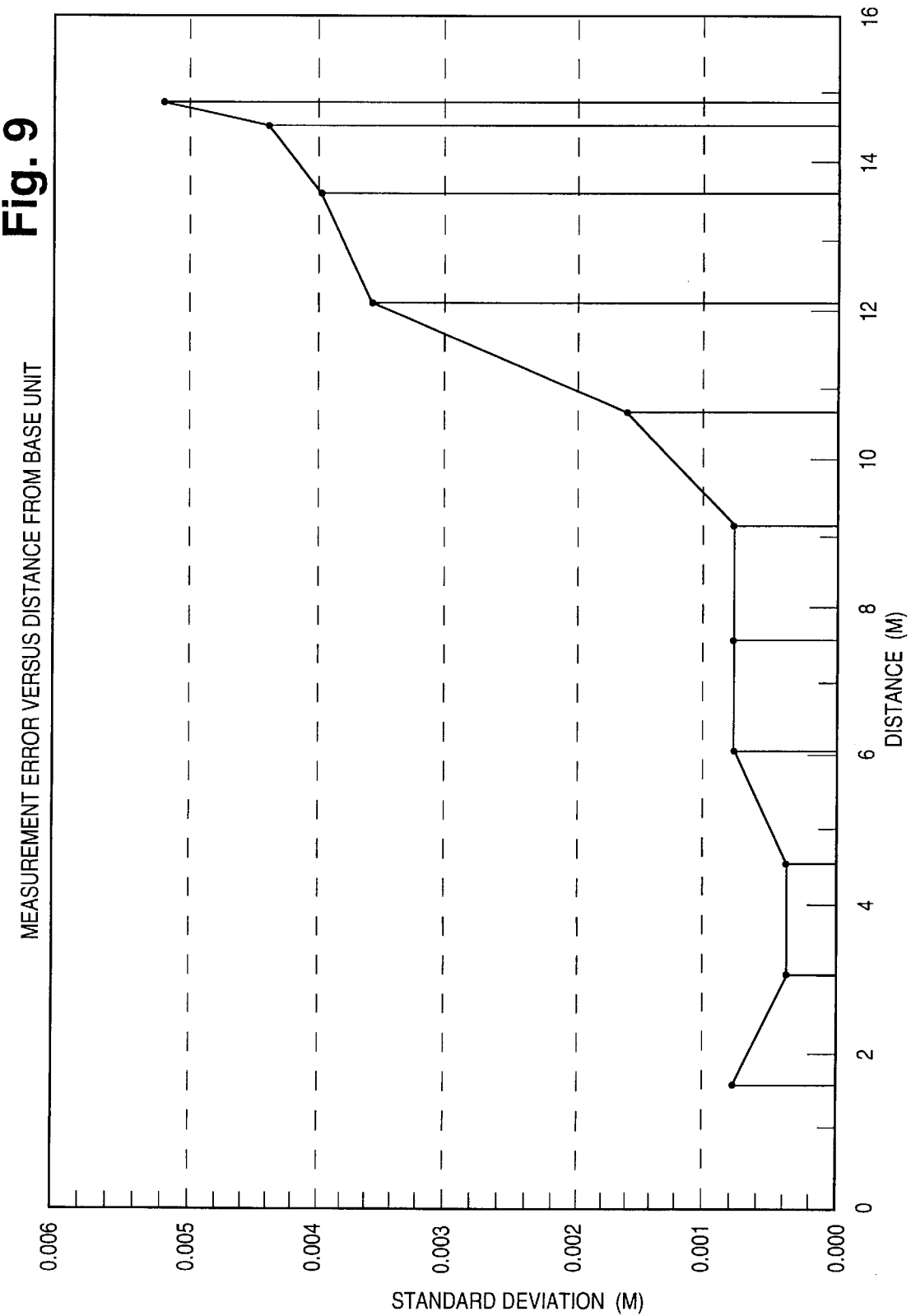

PORTABLE RANGING SYSTEM FOR ANALYZING GAIT

STATEMENT REGARDING FEDERALLY SPONSORED RESEARCH OR DEVELOPMENT

Research and development related to the present invention was funded by NIDRR, grants H133P20016 and H133E30007.

CROSS-REFERENCE TO RELATED APPLICATIONS

Not Applicable

BACKGROUND OF THE INVENTION

Analysis of a person's manner of walking, or gait, is known in the medical field. A person's freely elected walking speed is one of the better indicators of how well a person walks. Walking speed generally decreases in times of injury and pain and increases with recovery. For example, it has been shown that gait speed, cadence and stride length are gait parameters which continue to improve or increase as stroke patients recover. Gait speed, therefore, has been used to assess the effectiveness of different rehabilitation techniques for facilitating ambulatory recovery in stroke patients. In addition, gait parameters such as gait speed and stride length have also been utilized to assess the effectiveness of exercise programs for improving ambulation in the elderly. Moreover, gait parameters are useful to permit the proper fitting and adjustment of the alignment of lower limb prostheses. Thus, having means to analyze the interrelationship of gait parameters such as gait speed, cadence, and stride length is particularly useful for characterizing gait and correcting gait abnormalities.

Existing gait analysis systems, however, are typically very expensive, often costing well over a hundred thousand dollars, are complicated to use, not portable, require a dedicated staff of technicians to process the data obtained, and can take days to achieve the necessary data for gait analysis. Additionally, because of the high cost, gait analysis systems are typically housed only in dedicated laboratories of medical centers that are large enough and have enough financing to purchase and maintain such a gait analysis system.

The above limitations of existing gait analysis systems cause problems for the practitioner and patient alike. For example, patients are often required to travel long distances to get to the large medical centers having such laboratories in order to have gait analysis performed. Thus, in this day and age of managed health care where insurance companies are loath to pay for procedures they do not deem to be necessary, existing gait analysis systems, while a useful tool for improving ambulation, are often cost prohibitive to some patients.

One known prior art device for use with functional electrical stimulation has attempted to overcome the shortcomings of existing gait analysis systems. The Karcnik et al. device employed a transmitter unit worn by a subject, a receiver unit, and a host computer. The transmitter unit contained both an infrared transmitter and an ultrasound transmitter. When a patient begins walking using the Karcnik et al. system, the infrared and ultrasound transmitters simultaneously emit signals to the receiver unit. The infrared transmission triggers the receiver unit to begin counting and the ultrasound signal triggers the receiver unit to stop counting. The receiver thus counts during the time it takes for the ultrasound to travel from the transmitter to the receiver. The system is calibrated in centimeters or millimeters, and upon selection of a proper clock frequency, the hardware in the receiver can compute the distance between the two units as well as the velocity of the transmitter unit.

The Karcnik et al. device was not the first to use ultrasound to measure distance. For example, some Polaroid® cameras measure the time taken for an ultrasound pulse, emitted from the camera, to travel to the object being photographed and, after reflection, back to a sensor on the camera. The time of flight is then used to compute distance and change the camera settings accordingly.

In addition, ultrasound ranging has been used in commercial electronic measuring tapes. The Sonin® 150 is an example of such a device. The Sonin® employs an infrared emitter and an ultrasound receiver in a source unit and an infrared receiver and an ultrasound emitter in a target unit. Receipt of the infrared signal initiates an ultrasound pulse. The Sonin® is designed to initiate a new distance sample immediately upon receipt of the ultrasound pulse, or after a suitable period of time has passed without receipt of an ultrasound pulse. The Sonin® 150 repeats this process a number of times and then computes an average distance based on the timed receipt of the ultrasound pulses.

None of the above discussed devices and their teachings, however, overcome the shortcomings of existing gait analysis systems. Specifically, the Polaroid® cameras discussed above do not address the special problem of measuring and manipulating data related to a moving object. Moreover, such systems, even if they could analyze motion, have several drawbacks. For example, because such systems require the use of reflected signals, the ultrasound pulse must travel twice the distance. This is a problem because, assuming a point source, the magnitude of the pulse decreases in a manner inversely proportional to the square of the distance. In other words, the magnitude of the received pulse decreases at an increasingly higher rate the greater the distance the pulse must travel. In addition, the ultrasound pulse in a reflecting system may be scattered or absorbed by the reflecting surface. Reflecting systems also double the time of flight necessary for a single measurement.

For these reasons, direct ultrasound ranging systems, such as the Sonin® 150 discussed above were developed. The Sonin® 150, however, like the systems found in Polaroid® cameras, is only suited for measuring static distance. It is not capable of, nor does it address the special problems associated with, measuring and manipulating data related to a moving object. Moreover, since these devices are only capable of accurately measuring the distances to stationary objects, it does not matter if an ultrasound pulse is occasionally not received. If the Sonin® does not receive an ultrasound pulse for a period, it simply resends another pulse and repeats the process until enough pulses are received to perform the average distance calculation. When measuring a moving object, however, since distance is constantly changing, it is important that every triggered pulse be received.

While the Karcnik et al. device discussed above is capable of measuring motion, it, too, falls short of overcoming the shortcomings of existing gait analysis systems. For example, the Karcnik et al. device experiences problems receiving infrared transmissions due to the roll and pitch of patients as they walk (or limp) with the infrared emitter (or receiver) on their person. If an infrared signal is not received, the corresponding ultrasound signal, while it may be received, is not properly counted and is thus lost. This results in a corruption of the data received and used for processing, and thus an overall inaccurate system.

In addition, the results obtained by the Karcnik et al. device have further injected error due to its failure to compensate for the effects of temperature on the speed of sound. Furthermore, the Karcnik et al. system performs its counting via extensive external hardware, increasing the system cost and complexity.

BRIEF SUMMARY OF THE INVENTION

In accordance with the present invention the disadvantages found in existing gait analysis systems, as discussed above, have been overcome. More particularly, a portable ranging system is disclosed which is capable of analyzing gait. The system comprises as an infrared emitter, an infrared receiver, an ultrasound emitter, an ultrasound receiver, and system circuitry.

Upon actuation, the circuitry begins counting and simultaneously causes the infrared emitter to emit infrared light into a ranging area. In one embodiment, the infrared emitter "floods" the ranging area with light, and can comprise an infrared strobe. The infrared receiver receives the infrared light, and in response, emits an ultrasound pulse. The ultrasound pulse is next received by the ultrasound receiver, which in turn causes the system circuitry to stop counting. The circuitry then can use the count data to calculate the time of flight of the ultrasound pulse and thus the distance between the ultrasound emitter and the ultrasound receiver.

The above counting process is repeated for a plurality of constant time periods, enabling the distance between the ultrasound emitter and the ultrasound receiver to be calculated for each time period. The distance data can then be differentiated by the circuitry to obtain the velocity of either the ultrasound emitter or ultrasound receiver, whichever is moving.

In one embodiment, the infrared emitter and ultrasound receiver are housed in a self-contained base unit, the infrared receiver and ultrasound emitter are housed in a self-contained transponder (which is worn by a walking subject), and the circuitry includes a computer terminal having a display. Once the velocity data is obtained (as discussed above) for the walking subject, certain gait parameters, such as gait speed, cadence, step time, step length, peak-to-peak variation, and time to achieve steady state walking, are displayed.

The system may also include means for preventing noise received by the system and/or already present in the system from falsely triggering the receipt of an ultrasound pulse. In one embodiment, a time varying adaptive threshold is used for this purpose.

These and other advantages and novel features of the present invention, as well as details of an illustrated embodiment thereof, will be more fully understood from the following description and drawings.

BRIEF DESCRIPTION OF THE SEVERAL VIEWS OF THE DRAWING

FIG. 9 is a graphical representation of how the measurement error varies with distance for the embodiments of the base unit and transponder of FIGS. 3 and 7, respectively.

DETAILED DESCRIPTION OF THE INVENTION

Figure 1:
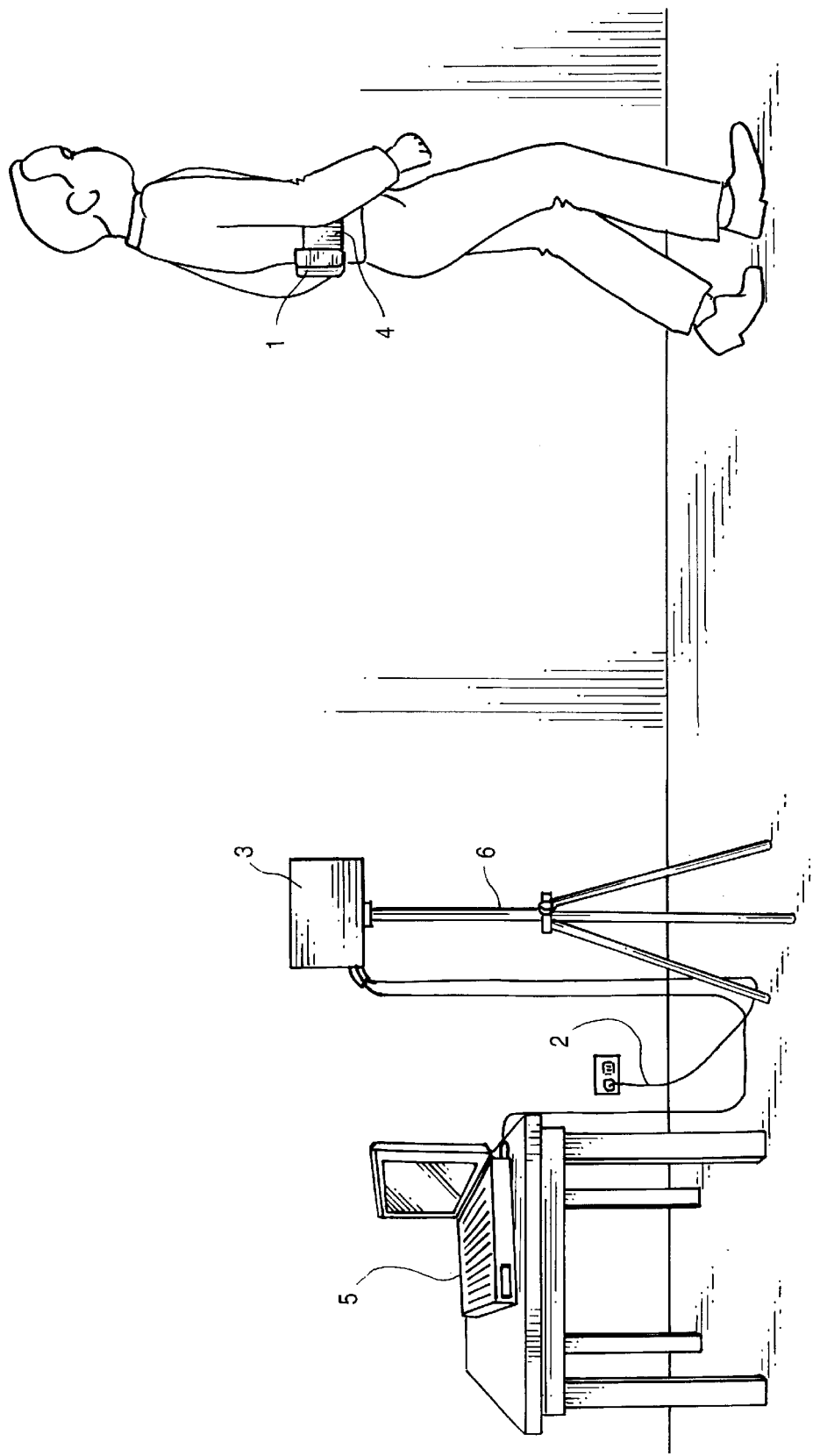
FIG. 1 illustrates one embodiment of a portable gait analysis system built in accordance with the present invention.

FIG. 1 illustrates one embodiment of a portable gait analysis system of the present invention having a transponder 1, a base unit 3, and a computer terminal 5. During gait analysis, the transponder 1 is worn by the subject, usually posteriorly on the midline of the body at the approximate level of the body center of mass (e.g., sacral (S-2) level). For this purpose, a modified neoprene jogging belt 4 may be used to mount the transponder 1, which is battery powered. The base unit 3 is mounted on a tripod 6 at approximately the same height level as the transponder 1 worn by the subject. While the base unit 3 is shown as powered by an AC cord 2, it should be understood that the base unit 3 may also be battery powered if desired.

As the subject walks away from the base unit 3, the transponder 1 and the base unit 3 cooperate to display in real time on the computer terminal 5 the subject's forward progression. At the end of the walking trial, the data obtained by the base unit is used by the computer terminal 5 to create and display an instantaneous velocity profile, or gait velocigram (GVG), for that trial. From the GVG, gait parameters such as speed, cadence, step length, step time, peak-to-peak variation and time to achieve steady state walking are calculated and displayed by the computer terminal 5. From this information and the GVG, which are generated in more or less real time, a practitioner is able to readily ascertain the subject's gait pathologies.

Figure 2:
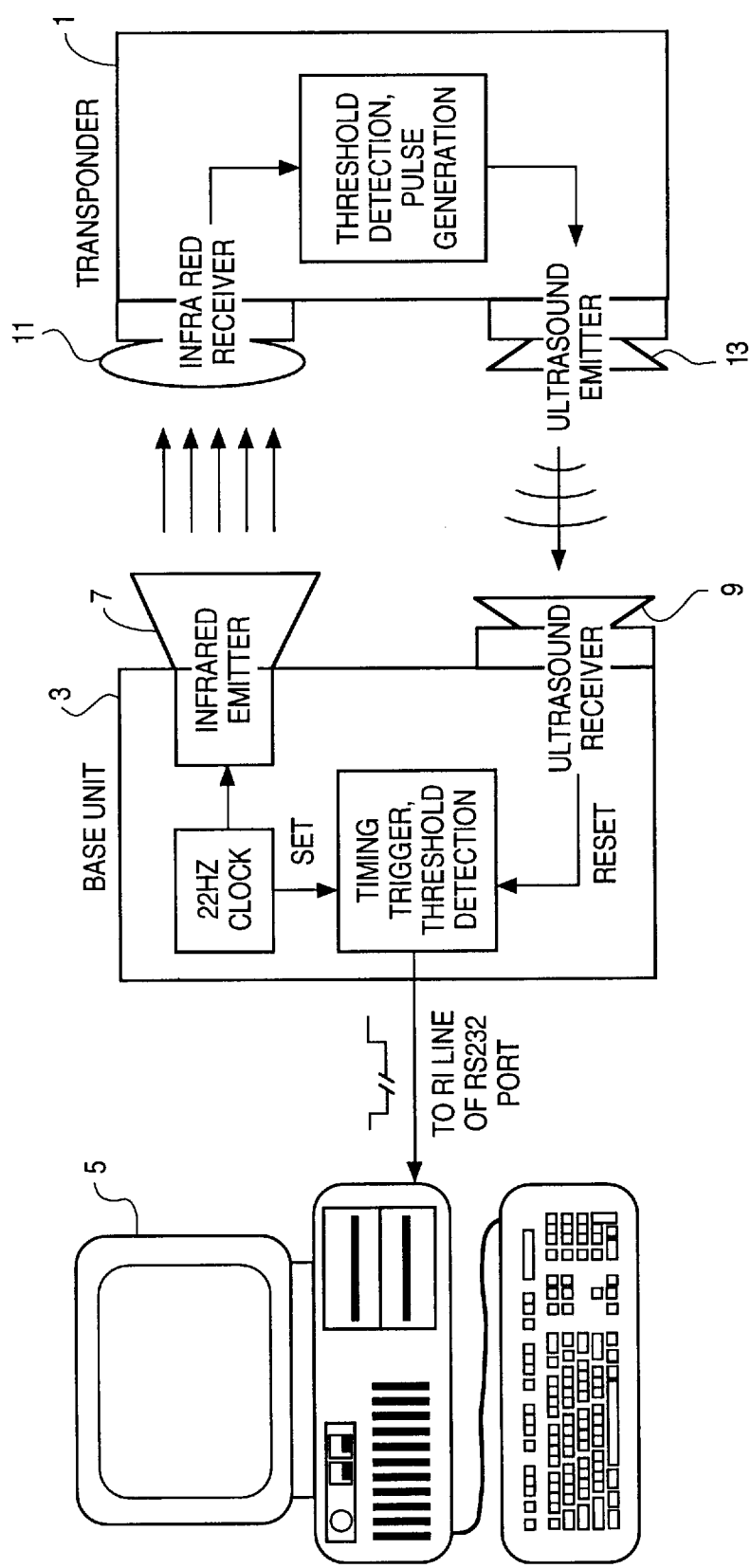
FIG. 2 is a block diagram of one embodiment of the gait analysis system built in accordance with the present invention.

FIG. 2 is a block diagram of one embodiment of the gait analysis system built in accordance with the present invention. The base unit 3 has an infrared emitter 7 and an ultrasound receiver 9. The transponder 1 has an infrared receiver 11 and an ultrasound emitter 13. In operation, the base unit 3 emits an infrared pulse from the base unit 3 at a constant frequency. At the same time the base unit 3 emits an infrared pulse, it also triggers the computer terminal 5 to start a counter. The transponder 1 in turn receives the infrared pulse via the infrared receiver 11 and triggers the ultrasound emitter 13 to emit an ultrasound pulse back to the ultrasound receiver 9 of the base unit 3. The arrival at the base unit 3 of the ultrasound pulse triggers the computer terminal 5 to stop counting. In accordance with one embodiment of the present invention, as explained more fully below, the computer terminal 5 uses an interrupt driven software routine to perform the counting. The computer terminal 5, being calibrated for a known number of counts per second, then converts the measured count into the time of flight for the ultrasound pulse.

Because the infrared pulse travels at the speed of light, the time between the emission of the infrared pulse and receipt by the transponder 1 can be considered to be instantaneous. The ultrasound pulse, however, travels at the speed of sound in air, which is dependent on both the relative humidity and temperature. While the effects due to humidity can be ignored, the effects due to temperature cannot if an accurate system is desired in every case. Thus, before making use of the time of flight data for the ultrasound pulse as determined by the computer terminal 5, the effects of temperature should be taken into account by the system.

The influence of the temperature is given by the following equation:

$$\text{speed of sound } (m/s) = 331 + (0.6)(\text{Temp.})(°C.)$$

At room temperature (22° C.), the speed of sound is approximately 344 meters per second. By calibrating for the speed of sound in air, the time of flight for the ultrasound pulse to travel from the transponder 1 to the base unit 3 can be converted by the computer terminal 5 into a measurement of the distance between the base unit 3 and the transponder 1. This is achieved using the following equation:

$$\text{Distance} = (\text{Speed})(\text{Time})$$

The computer terminal then stores the raw count and associated calibration information for later processing.

Because the system makes a distance measurement at a constant sampling rate, a measure of how distance changes over time (i.e., velocity) can then be obtained. The use of constant sampling or triggering rate, however, imposes a maximum distance that can be measured by the system. This limitation is due to the maximum distance that sound can possibly travel within the designated sample interval. A sampling frequency of 22 Hz is acceptable for use by the present invention because it allows a range of approximately 15 meters to be measured and it is almost four times the highest frequency component generally associated with normal walking (6 Hz), thus satisfying the Nyquist criterion. It should be understood, however, that other sampling rates may be used.

Figure 3:
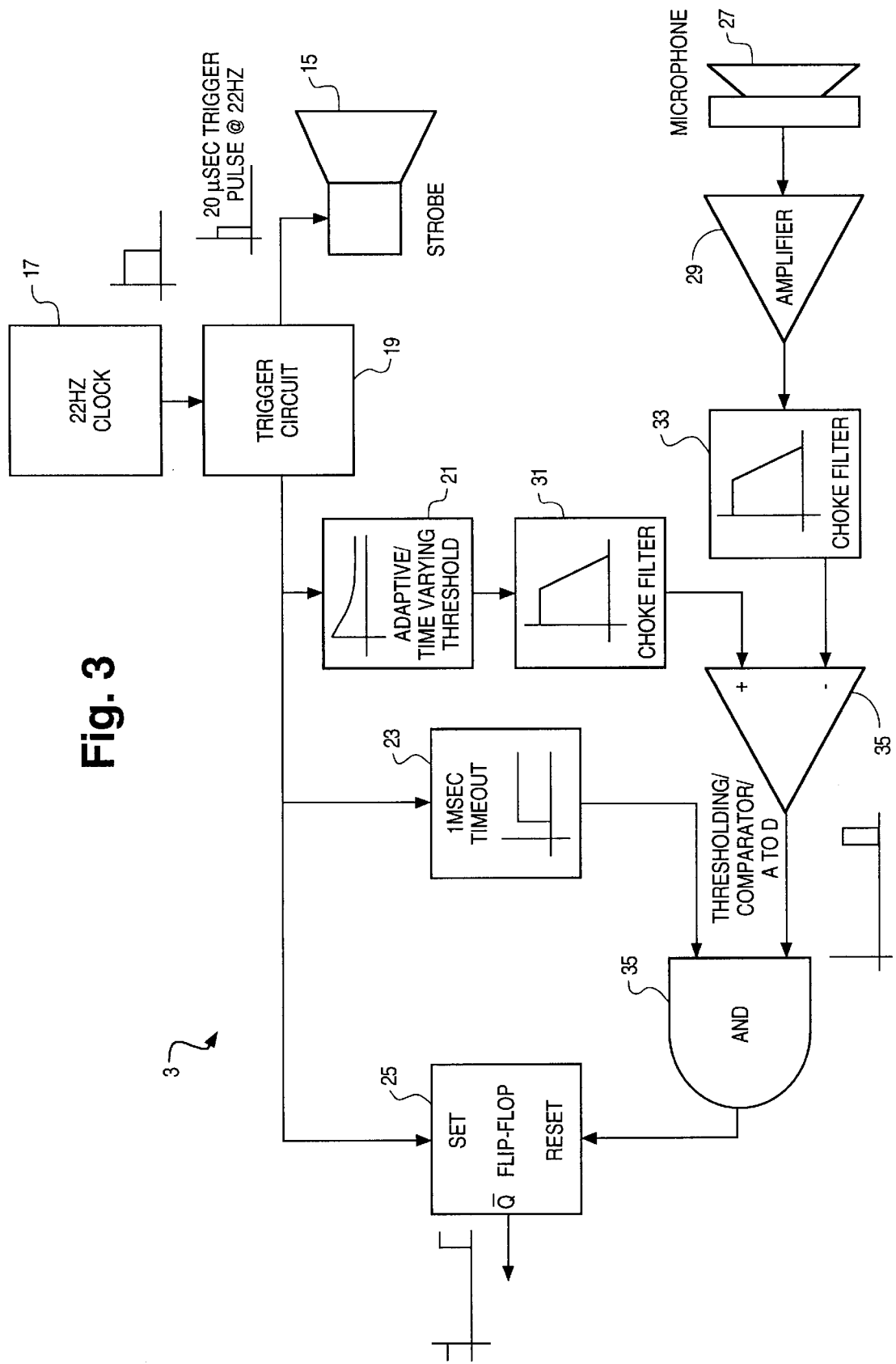
FIG. 3 is a block diagram of the base unit control and computer interface built in accordance with one embodiment of the present invention.

FIG. 3 is a block diagram of the base unit 3 control and computer interface built in accordance with one embodiment of the present invention. The infrared emitter 7 of FIG. 2 is shown as a strobe 15 in FIG. 3. As mentioned above, the reliability of prior systems was poor because of the directional nature of infrared transmitters. Small changes in position of the infrared receiver/emitter, even at a distance of only 5 to 6 meters, often prevented the reception of the infrared pulse. Reliability was further limited by deterioration of the infrared pulse, which decreased in magnitude over distance to the point where it could no longer be detected.

Figure 4:
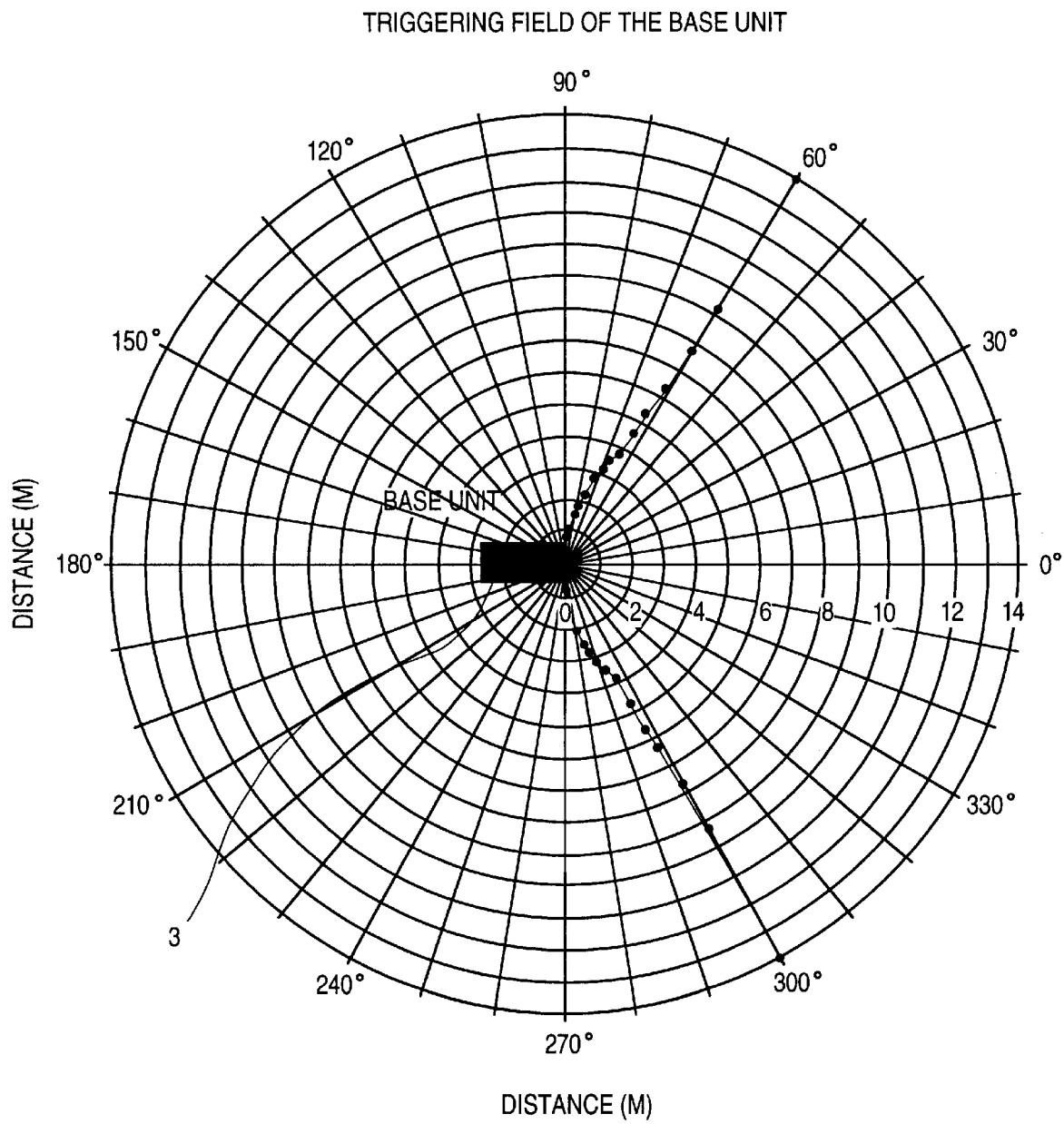
FIG. 4 is a polar plot of the receptive field of the base unit of FIG. 3.

These problems are overcome by using the infrared emitter 7 of FIG. 2 to "flood" the walkway or test area with high-intensity infrared light. As shown in FIG. 3, this flooding may be achieved by using an infrared pulse signal from strobe 15. FIG. 4 represents a polar plot of the area illuminated by the base unit 3 for the embodiment of the invention illustrated in FIG. 3. More specifically, FIG. 4 is a polar plot of the receptive field of the base unit showing the area that the base unit can illuminate with infrared light and still trigger and receive an ultrasound pulse from the transponder 1. As can be seen, at a distance of 14 meters, the base unit 3 is capable of triggering and receiving an ultrasound pulse even if the transponder 1 is at an angle of 60° from the direction to which the base unit 3 is facing. Flooding of the infrared light enhances the overall performance, reliability, and accuracy of the system.

In addition, flooding also enables the triggering of multiple transponders simultaneously, allowing the measurement of more than one parameter. Multiple receivers triggered by the same infrared pulse can enable triangulating on a transponder to obtain its coordinates in two or three dimensional space.

Referring again to the embodiment of FIG. 3, a clock 17 activates trigger circuit 19 once every, for example, 0.04545 seconds (at 22 Hz). The trigger circuit 19 in turn activates the strobe 15 to emit a high-intensity infrared pulse. At the same time the trigger circuit 19 triggers an adaptively time varying threshold 21. The varying threshold 21 is used to track the decreasing amplitude of the ultrasound signal with distance, allowing an ultrasound pulse, unlike prior systems, to be consistently and reliably detected at greater distance. If a constant threshold is used, it must be set above the level of any noise present in the system. Consequently, the range of a system using a constant threshold is limited to the distance at which the magnitude of the ultrasound pulse is slightly greater than that of the noise signal.

Figure 5A:
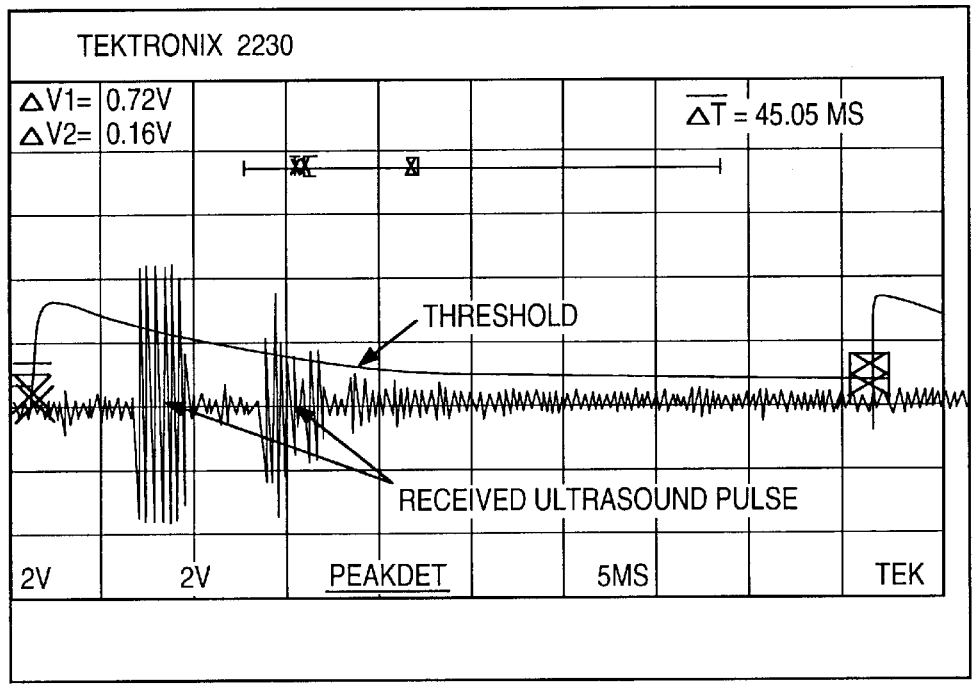
FIGS. 5a and 5b illustrate oscilloscope plots showing the varying threshold and received ultrasound pulse at approximately 2 meters and 15 meters, respectively, in accordance with the embodiment of FIG. 3.

The magnitude of the noise level in the system is dependent on the elapsed time since the last trigger cycle by the trigger circuit 19. The noise occurs with greatest magnitude immediately following emission of the infrared pulse and then diminishes with time. The time period of high noise incidentally corresponds to the time period when the magnitude of the ultrasound signal is greatest, i.e., when the transponder 1 is close to the base unit 3. The noise in the system diminishes after a finite time period corresponding to a distance of two to three meters. FIG. 5a illustrates an oscilloscope plot showing the variable threshold and received ultrasound pulse at a distance of approximately two meters.

Figure 5B:
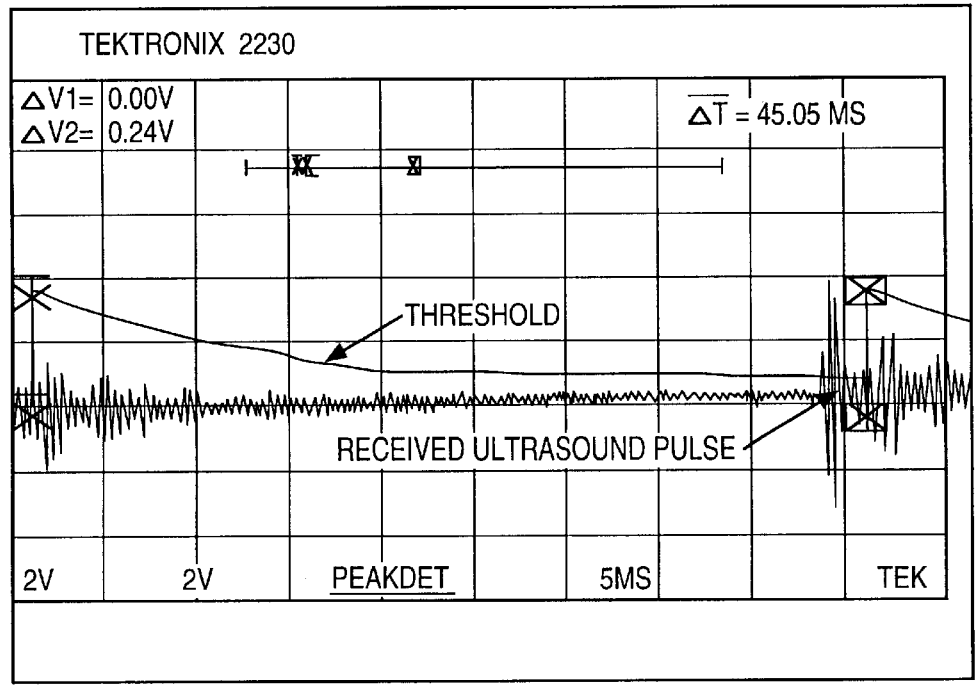

Beyond this time period, there is very little noise present in the system and much smaller magnitude ultrasound pulses can be readily detected. The adaptively time varying threshold 21 places the threshold above the level of noise when the transponder 1 is close to the base unit 3 and then gradually decreases its level to match the decreasing magnitude of the ultrasound pulse with distance. The magnitude of the ultrasound pulse decreases as an inverse square of distance. FIG. 5b illustrates an oscilloscope plot showing the time varying threshold and received ultrasound pulse at a distance of approximately 15 meters. As is apparent, the threshold decreases as the noise dies out. The declining threshold, therefore, serves to eliminate the effects of noise that occurs: (1) when the transponder 1 is close to the base unit 3 due to the infrared pulse generation; and (2) when the transponder 1 is at a distance from the base unit 3 due to "wrap-around" from the ultrasound pulse of the previous sample. Like the "flooding" discussed above, the varying threshold enhances the overall performance, reliability, and accuracy of the system.

Referring again to FIG. 3, in addition to triggering the strobe 15 and the varying threshold 21, the trigger circuit 19 also triggers a timeout period 23 of, for example, 1 millisecond. The timeout period 23 counteracts the spike that occurs following the emission of the infrared pulse. The trigger circuit 19 also sets flip-flop 25, which in turn indicates to the computer terminal 5 to begin counting.

An ultrasound pulse is received from the transponder 1 via the ultrasound receiver 9 of FIG. 2, which is shown as microphone 27 in FIG. 3. The received ultrasound pulse is amplified by amplifier 29. The varying threshold signal and the ultrasound pulse are then fed through choke filters 31 and 33, respectively. Comparator 35 compares the threshold signal at its positive input and the signal at its negative input. When the signal at the negative input is greater than the varying threshold signal at the positive input, indicating receipt of an ultrasound pulse, the comparitor 35 outputs a logic 1. This logic 1 is then fed through AND gate 35 which in turn outputs a logic 1 and causes the resetting of flip-flop 25. The resetting of flip-flop 25 causes the computer terminal 5 to stop counting.

Figure 6:
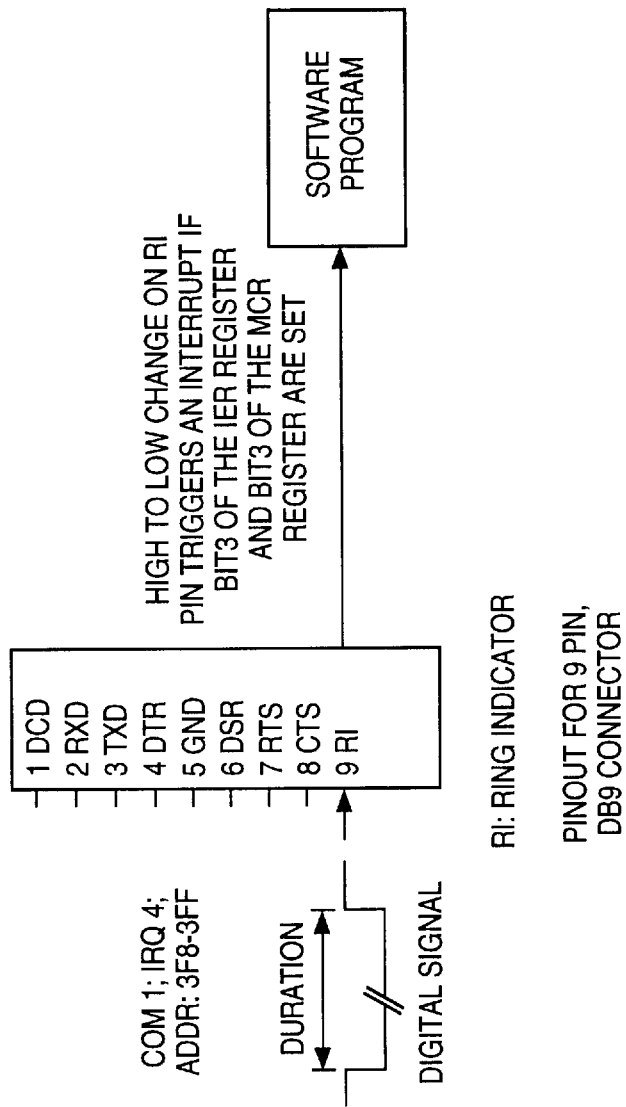
FIG. 6 shows the RS 232 communication port of the computer terminal used to receive signals from the base unit of FIG. 3.

FIG. 6 shows the RS232 communication port of the computer terminal 5 which is used to receive signals from the base unit 3 in the embodiment of FIG. 3. The flip-flop 25 of FIG. 3 signals the ring indicator (RI) line of the RS232 communication port, which in turn initiates an interrupt driven software routine when it goes from high to low. The software routine of computer terminal 5 computes the time of flight of each ultrasound pulse from the count rates as calibrated for the speed of sound.

Figure 7:
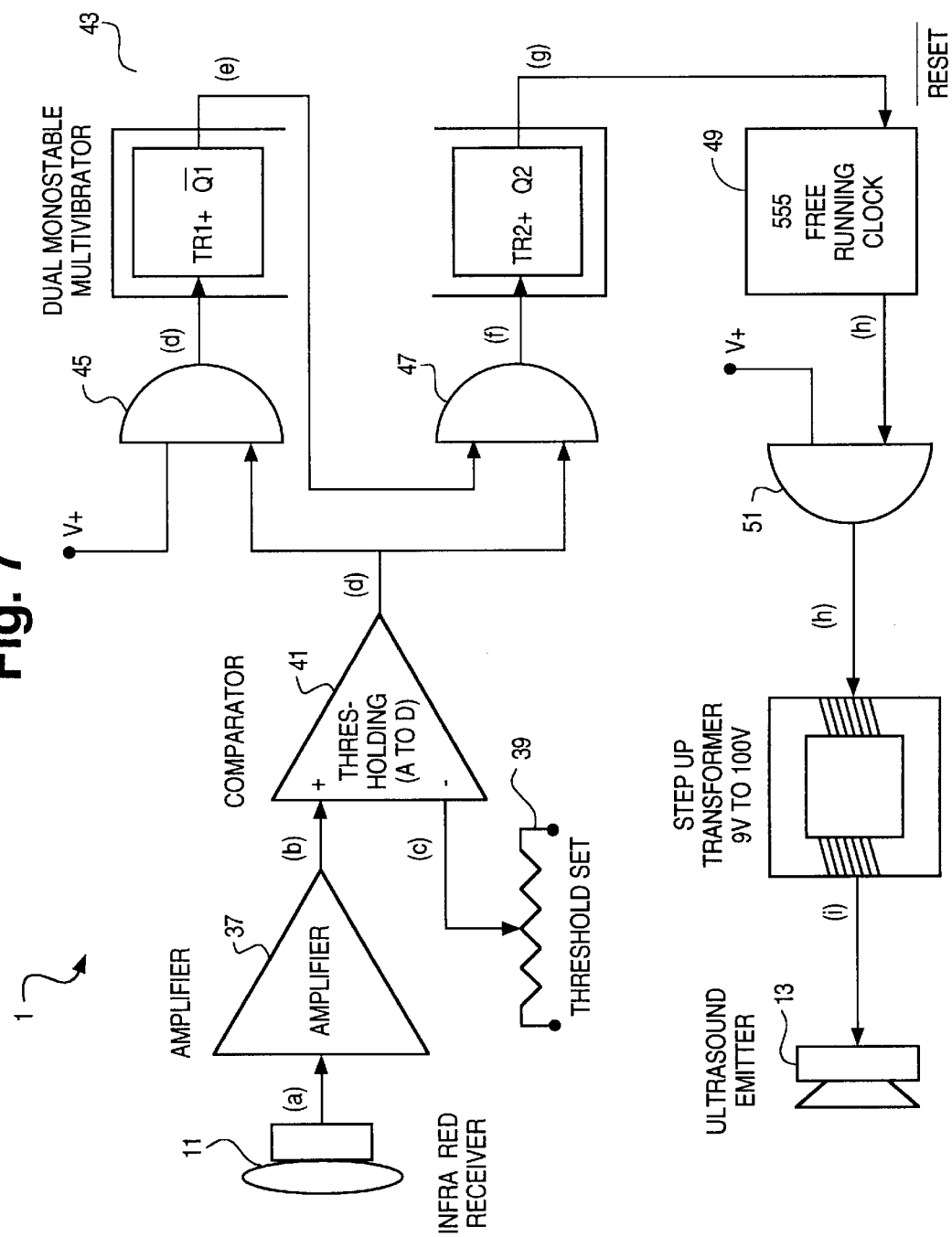
FIG. 7 is a block diagram of the transponder circuitry built in accordance with one embodiment of the present invention.

FIG. 7 is a block diagram of the transponder 1 circuitry built in accordance with one embodiment of the present invention. The magnitude of the infrared pulse ultimately received by the infrared receiver 11 decreases as an inverse square of distance in the same manner as the magnitude of the ultrasound pulse as discussed above. As a result, when the transponder 1 is close to the base unit 3, it receives a very large infrared pulse just as the base unit 3 receives a very large ultrasound pulse. At distance, the transponder 1 receives a very small infrared pulse that is just barely discernible against the background noise, just like the base unit 3 receives a greatly reduced ultrasound pulse. As such, the system can be characterized as having two states: close in and far out, with a gradual change from one to the other in between.

Figure 8:
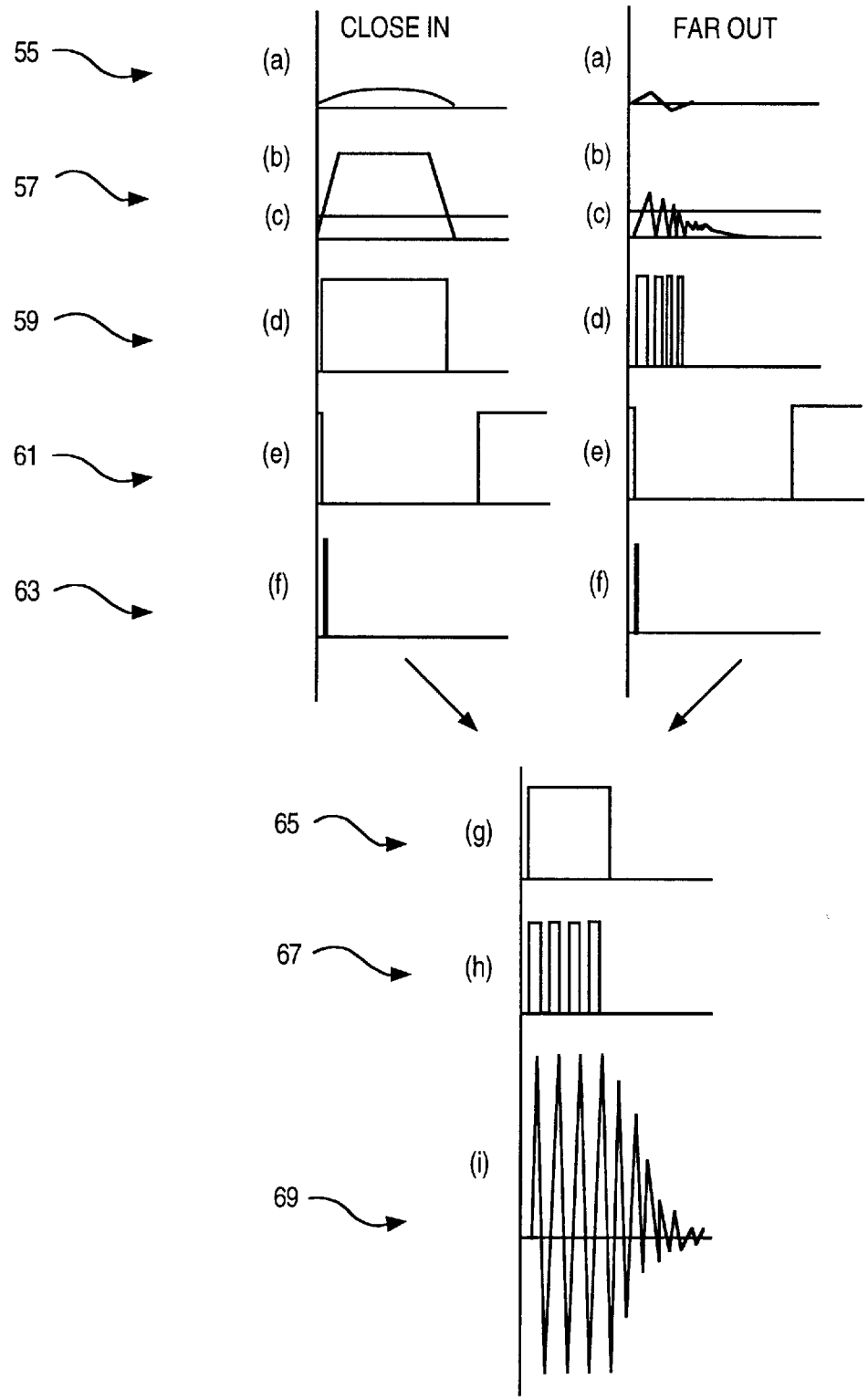
FIG. 8 is a diagram demonstrating the two state nature of the present invention for the embodiments of FIG. 7.
Figure 10A:
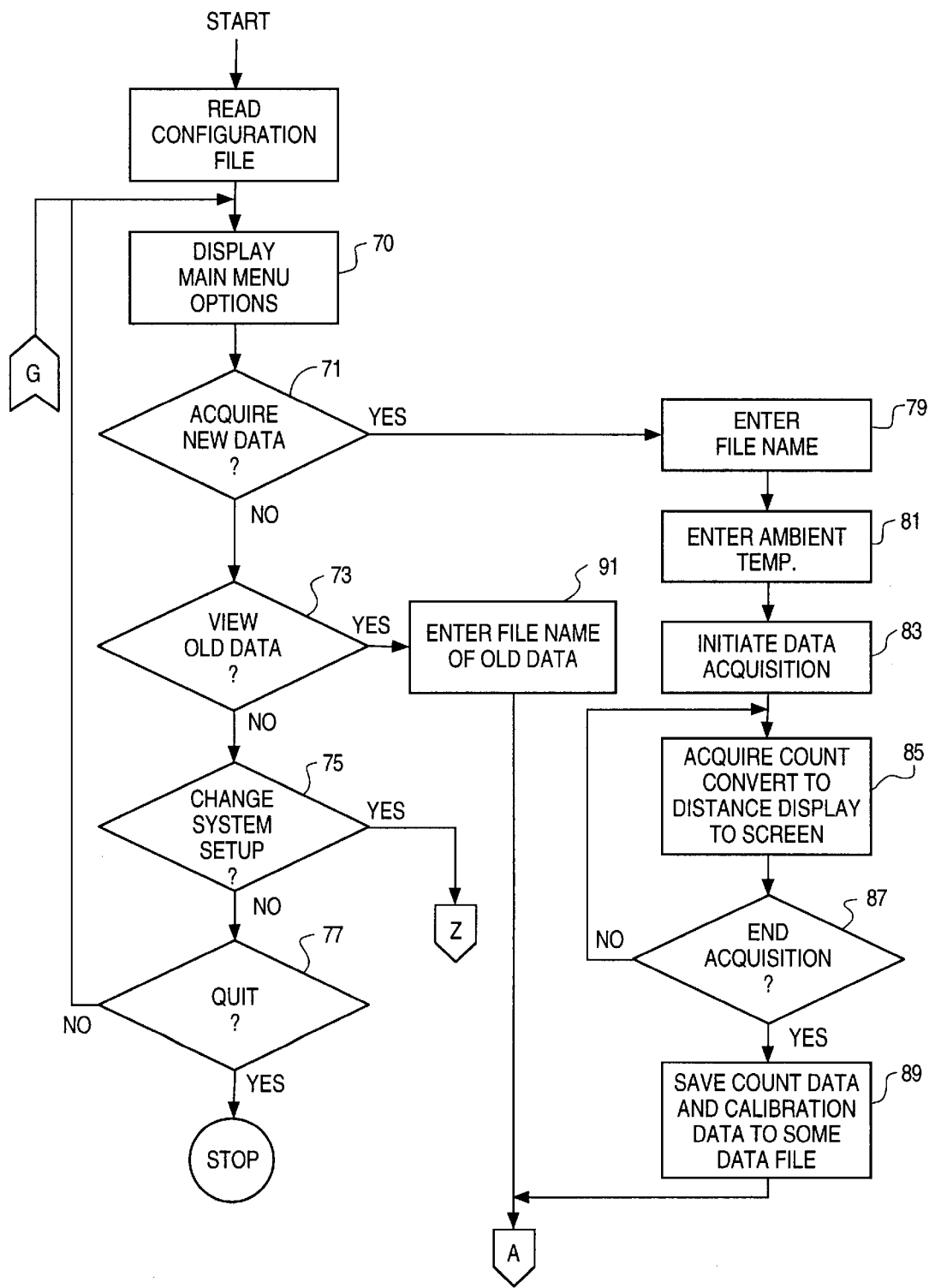
FIGS. 10a–j illustrate a flowchart of computer terminal software for operation in accordance with one embodiment of the present invention.
Figure 10B:
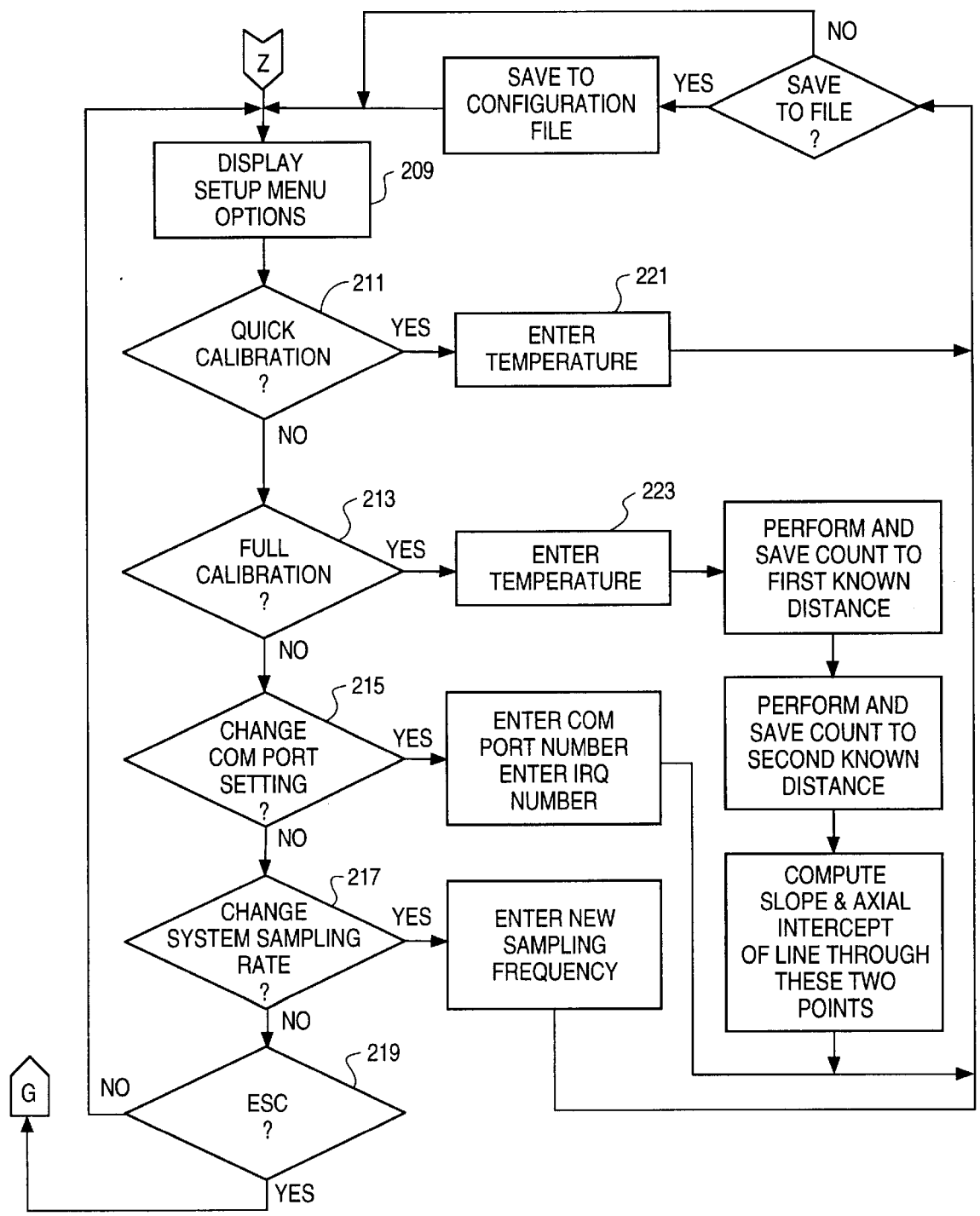
Figure 10C:
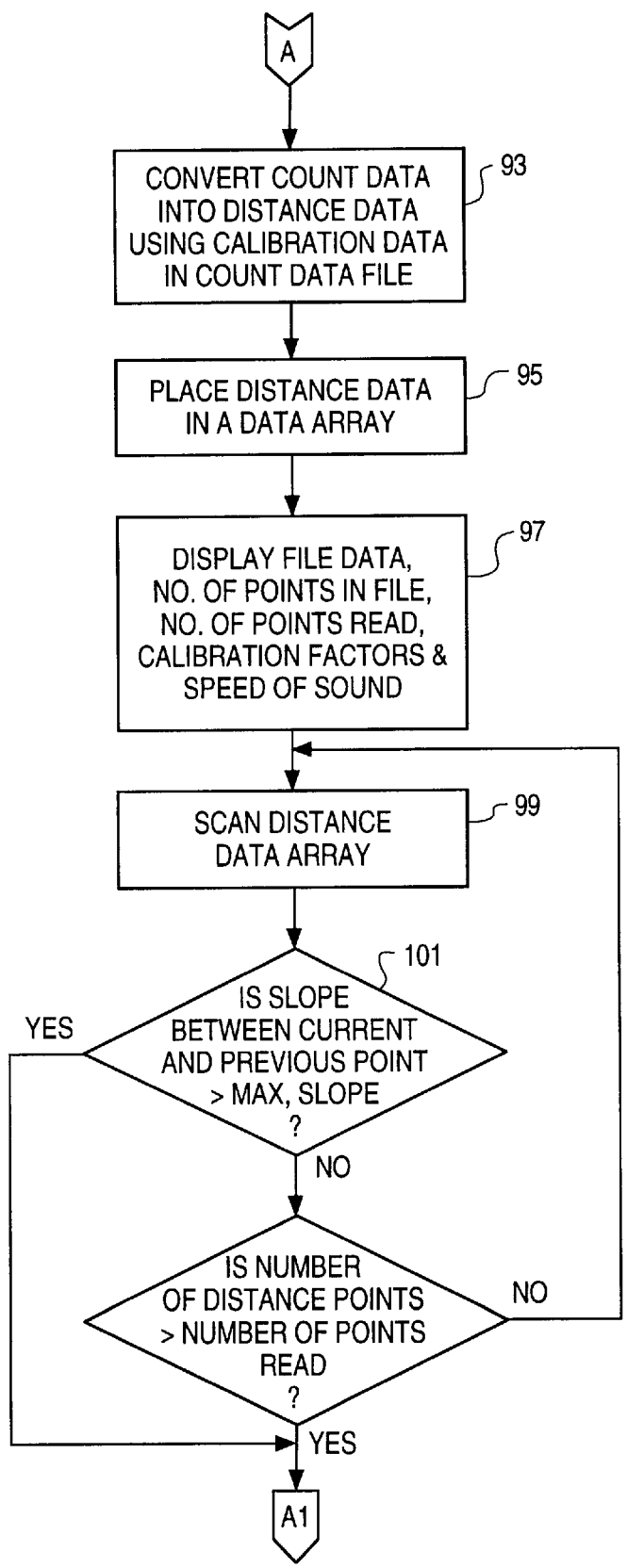
Figure 10D:
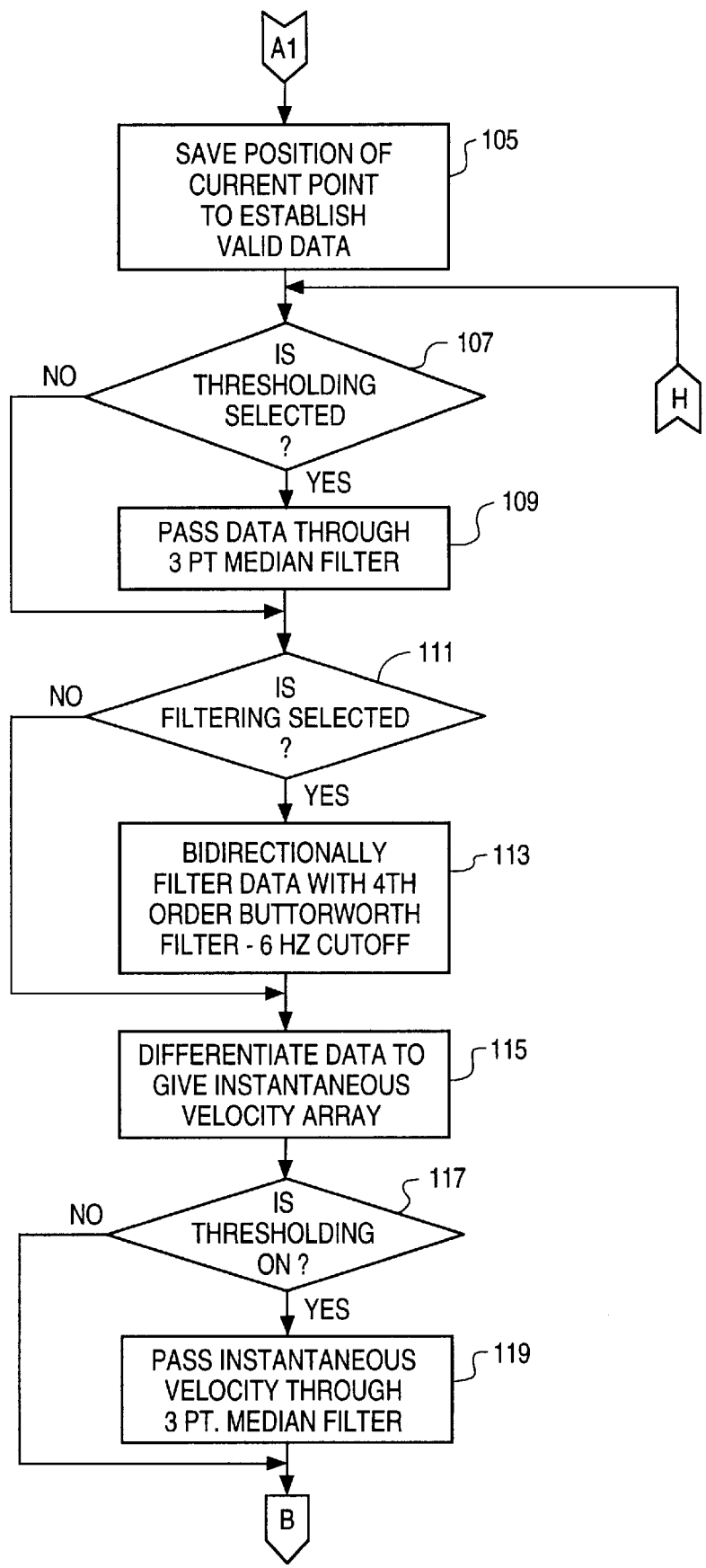
Figure 10E:
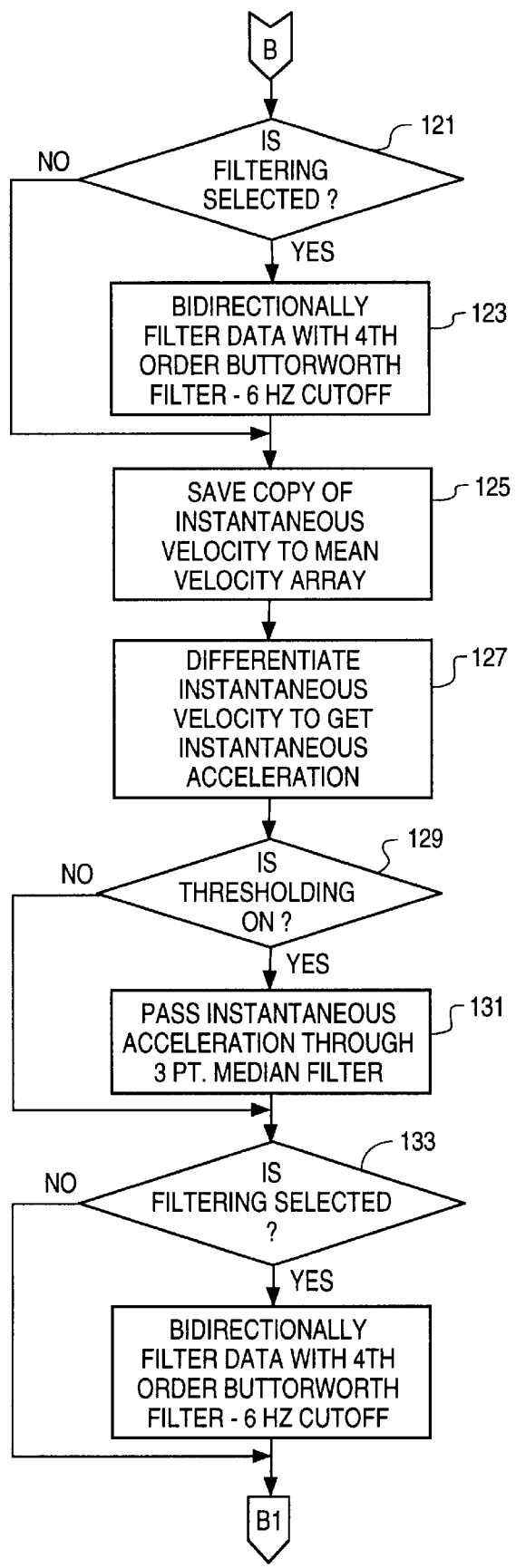
Figure 10F:
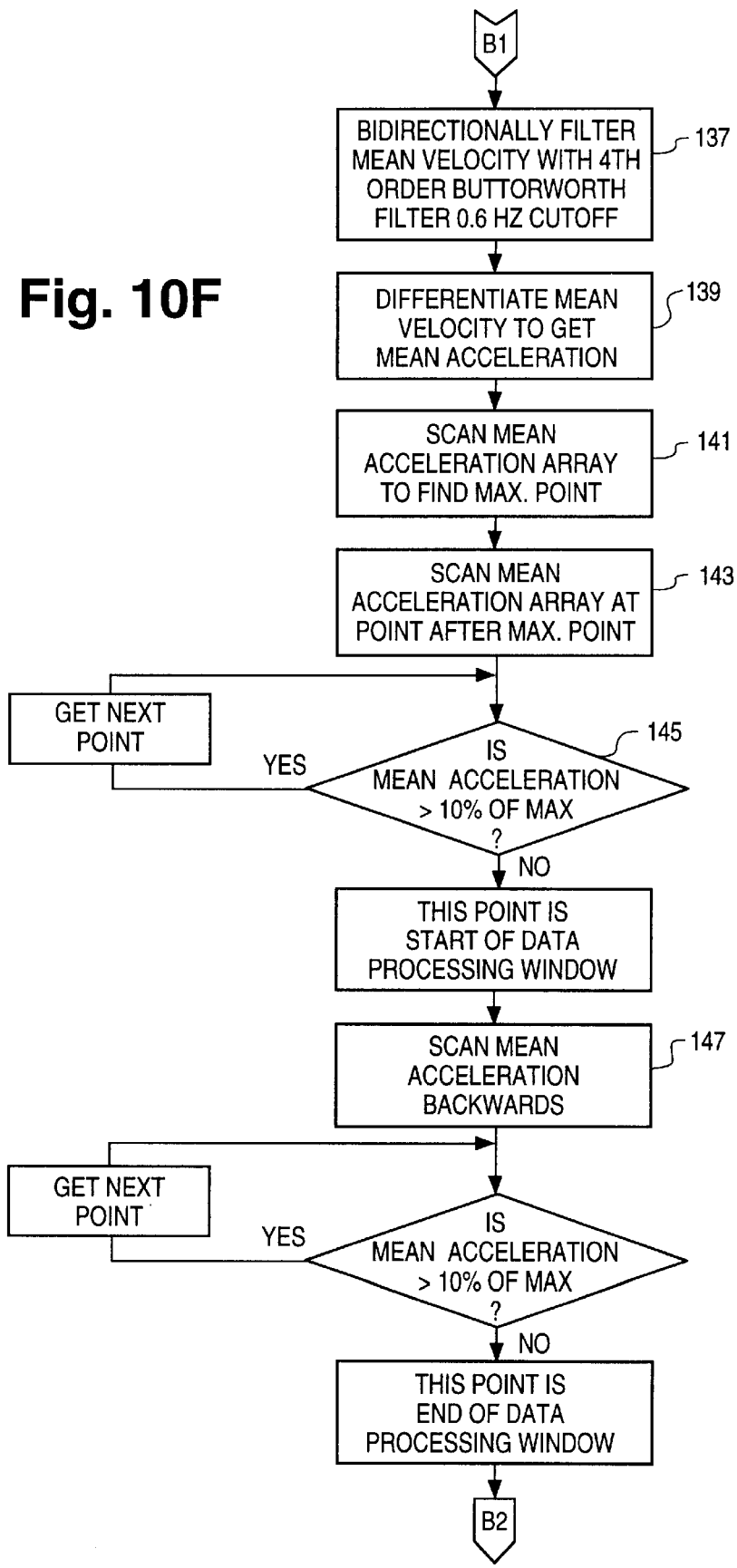
Figure 10G:
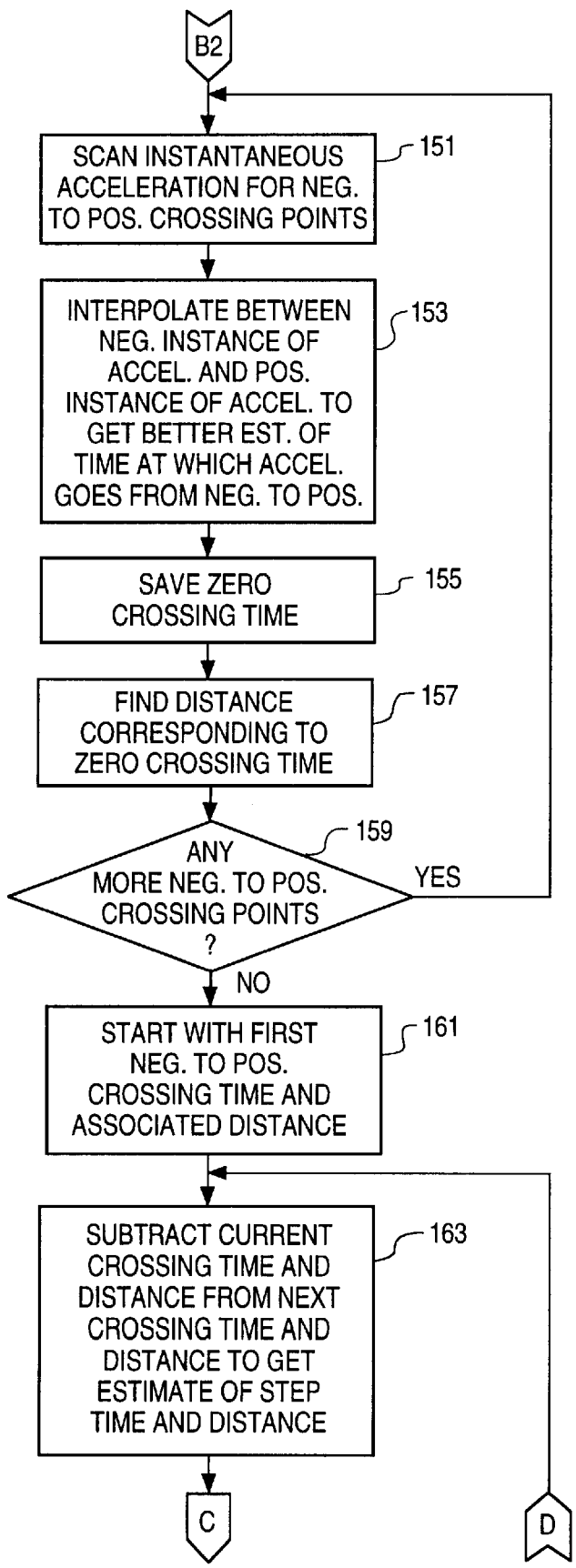
Figure 10H:
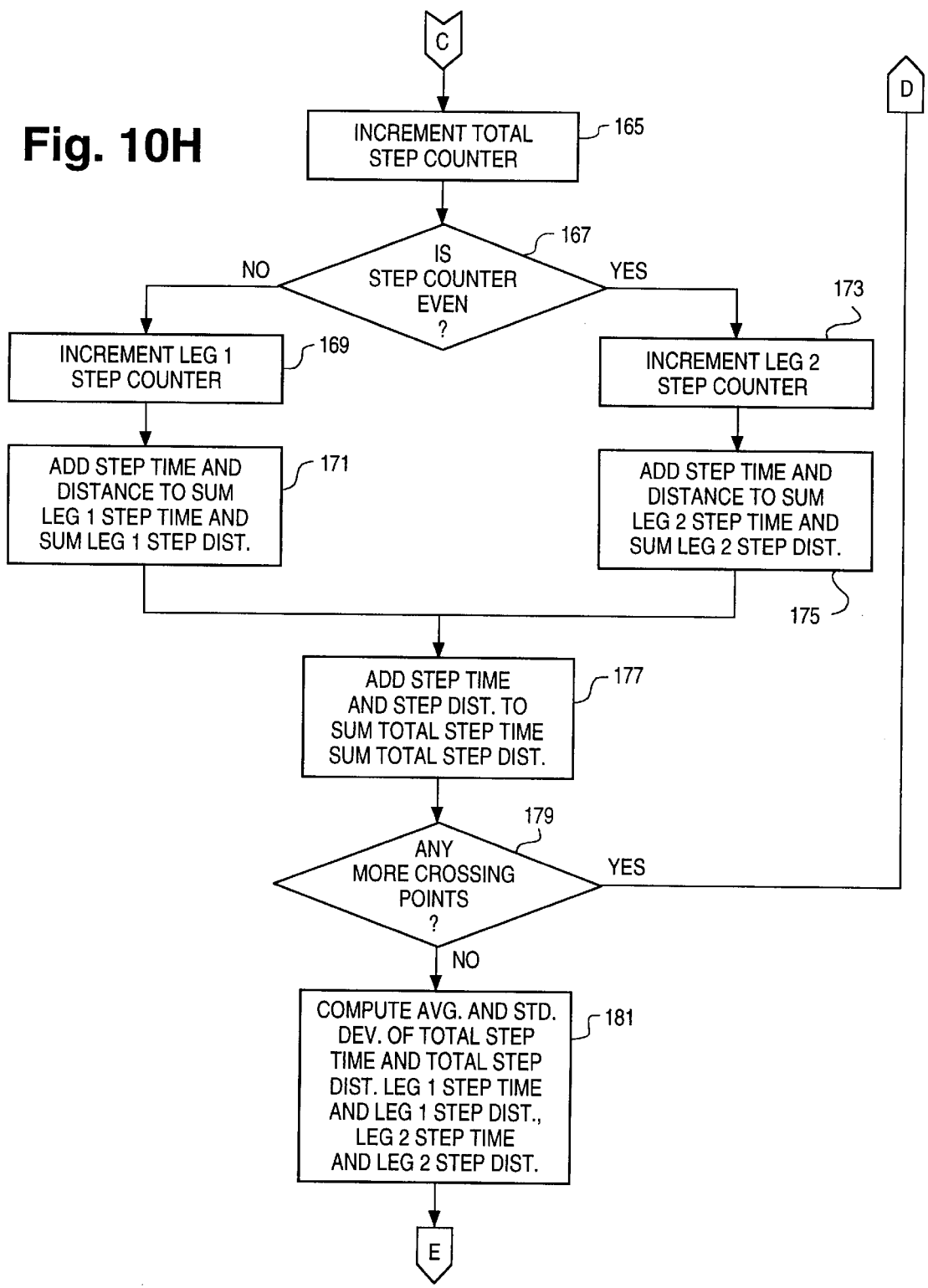
Figure 10I:
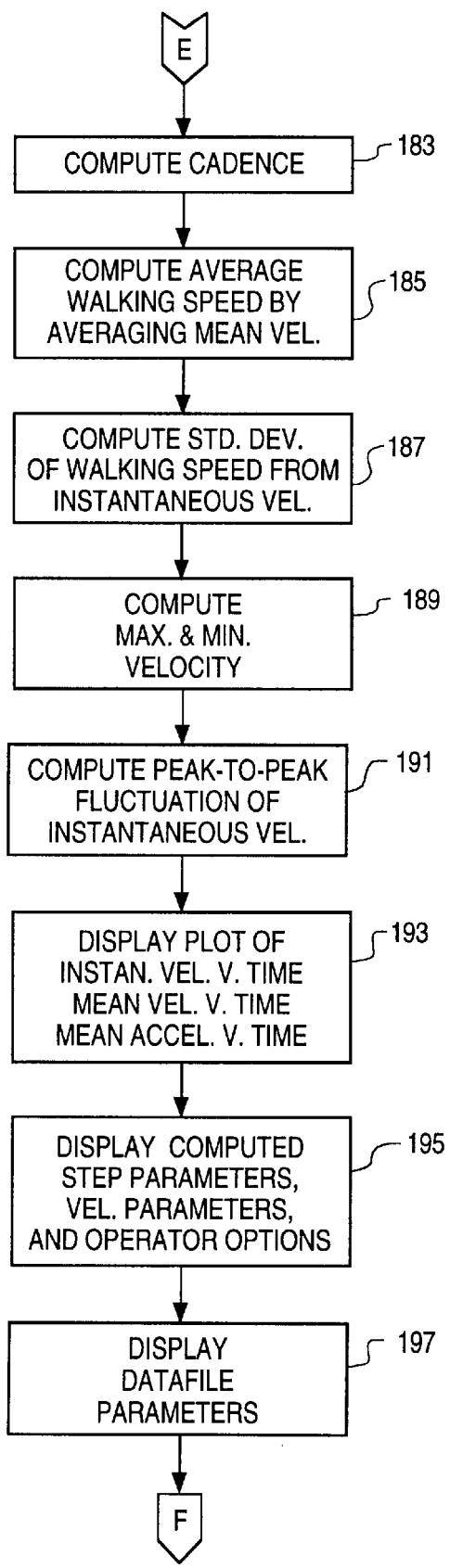
Figure 10J:
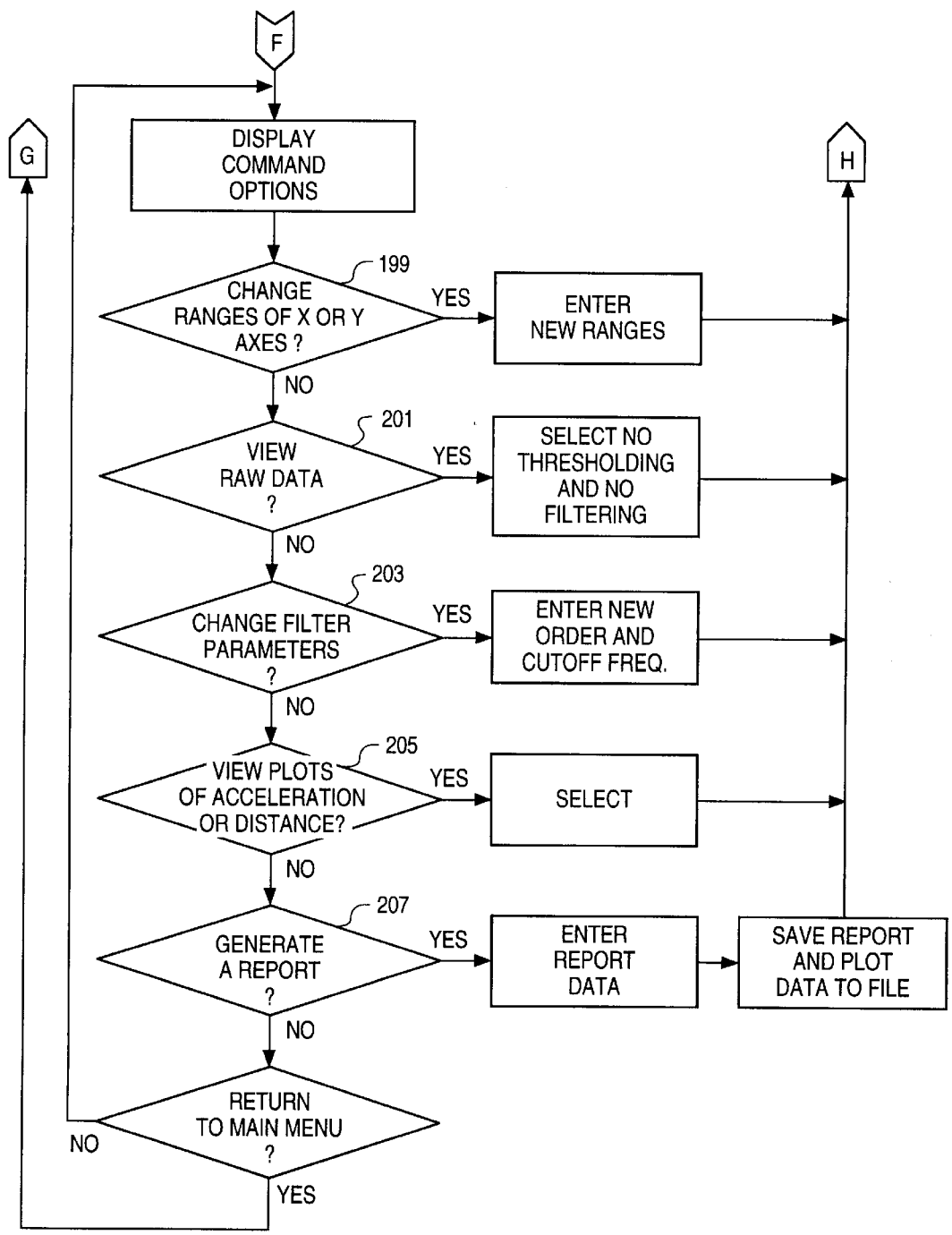

FIG. 7 is best described with specific reference to FIG. 8, which is a diagram of signals of the circuitry in FIG. 7. FIG. 8 demonstrates the two state nature of the system. The transponder 1 of FIG. 7 uses a constant threshold. Specifically, an infrared signal (a) received by infrared emitter 11 (see reference numeral 55 of FIG. 8) is amplified by amplifier 37. The amplified signal (b) is then compared to constant threshold 30 (c) via comparator 41 (see reference numeral 57 of FIG. 8). When the amplified signal (b) is greater than the constant threshold (c), the output of the comparator 41 (d) is set high, else it is set to ground (see reference numeral 59 of FIG. 8). The output of the comparator 41 (d) is used to set two time windows using a dual monostable multivibrator 43. When the output to AND gate 45 goes high (i.e., when the output of comparator 41 is high) the first time window (e) is set (see reference numeral 61 of FIG. 8). This first time window provides a time out period during which no other events detected at the input can trigger the circuitry to emit an ultrasound pulse. In other words, this time out period enables the circuitry to detect the small infrared pulses at distance and still preclude the increased noise that immediately follows the infrared pulse from triggering further events.

The output of comparator 41 is also sent through AND gate 47. The output (f) of AND gate 47 (see reference numeral 63 of FIG. 8) triggers a second time window to control the number of pulses in the pulse train (g) (see reference numeral 65 of FIG. 8) hitting the ultrasound emitter 13. Pulses are generated by clock 49 at a rate of, for example, 32 Khz. The pulse train can have, for example, 3–6 pulses. The pulse train (h) (see reference numeral 67 of FIG. 8) is sent through AND gate 51, the output of which is amplified by the transformer 58 to, e.g., 100 V to hit the piezoelectric ultrasound crystal. The transformer 53 should be matched to the ultrasound emitter 13 to ensure that the output of transformer 53 (i) (see reference numeral 69 of FIG. 8) can switch at a frequency needed to allow the emitter to go into resonance.

As mentioned above, the present system can be considered to have two states: close in and far out, with a gradual change from one to the other in between. FIG. 9 is a graphical representation of how the measurement error varies with distance for the embodiments of the base unit 3 and transponder 1 found in FIGS. 3 and 7, respectively. The standard deviation associated with the distance measurement is less than 1 mm out to about 10 meters. It then rises to a maximum of 5 mm at approximately 15 meters.

Figure 11:
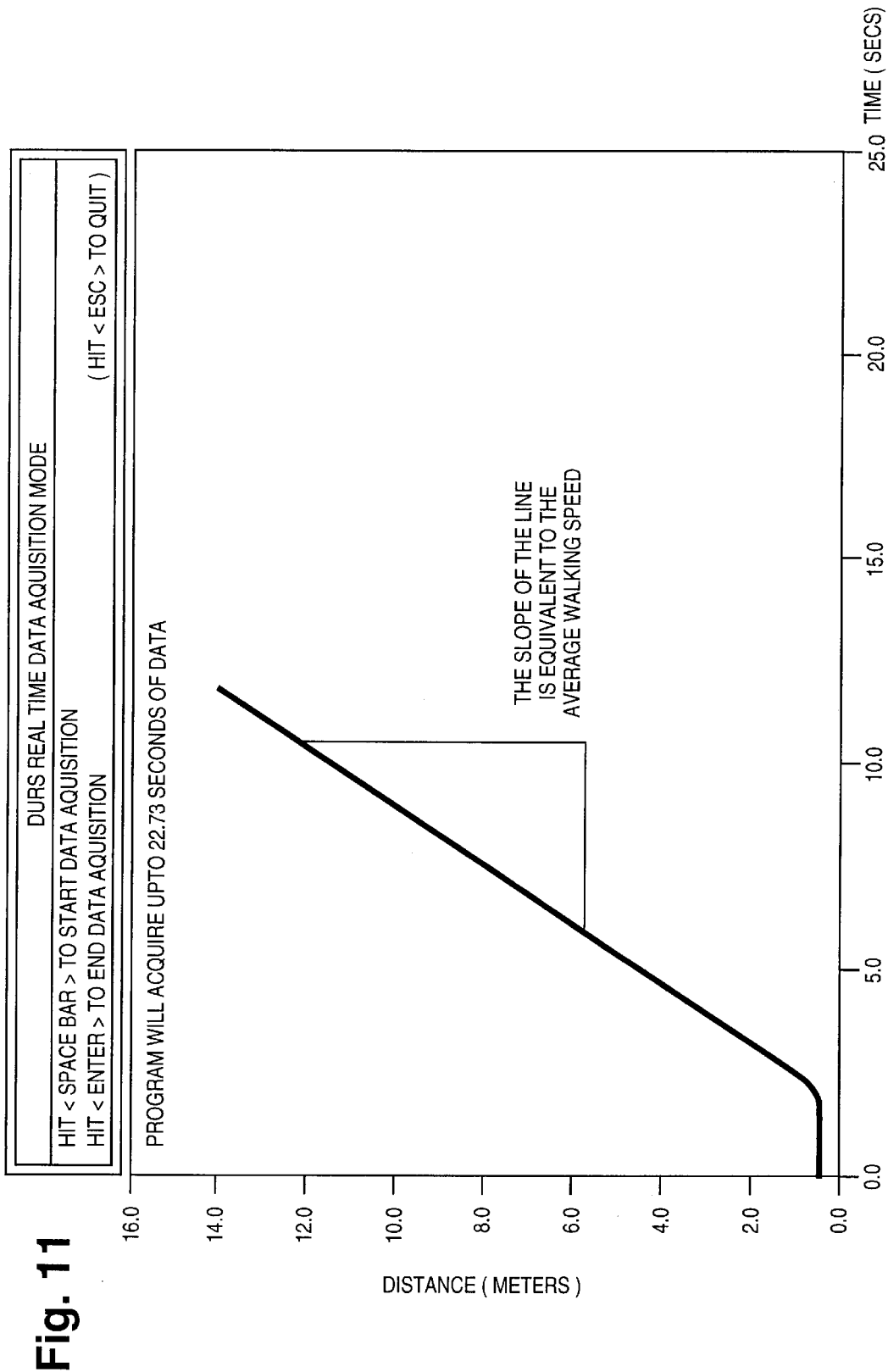
FIG. 11 illustrates one embodiment of a distance data display in accordance with the present invention.

FIGS. 10a–j illustrate a flowchart of computer terminal software for operation in accordance with one embodiment of the present invention. At the start of the program, the operator is presented with a main menu 70 providing several options. These options may include, for example, acquiring new data, viewing previously acquired data, changing the setup and calibration data, or quitting the program (see blocks 71–77). If the operator desires to acquire data, the operator selects that option. The operator is then prompted to enter a filename at a block 79. After entering a filename, the operator is presented with a real time data acquisition screen. Within this screen, a window opens prompting the user to enter the ambient room temperature to calibrate the system for the correct speed of sound (see block 81). It should be understood, however, that the program can be altered to permit a digital thermometer which, for example, can be part of the base unit 3, to automatically enter the temperature to bypass this manual step. Once the temperature is entered, the operator can proceed with data acquisition (see block 83). At this point, the operator instructs the subject to commence walking, right foot first, at their freely elected walking speed. As the subject moves away from base unit, the distance is continuously measured and displayed to the screen in real time until the end of data acquisition (see blocks 85 and 87). FIG. 11 illustrates one embodiment of how the distance data can be displayed to the screen in real time.

Once data acquisition is complete, the acquired count data, as well as the current calibration data (i.e., speed of sound, sampling frequency, and slope and axial intercept of line achieved from full calibration (see below)), are saved to a data file (see block 89). If the operator had decided at the main menu to view previously acquired data rather than selecting the acquiring new data option, the operator would have been prompted to enter the filename of the old data, which would have the old count data as well as the associated calibration data (see block 91). In either case, the data is now ready to be post-processed.

Post-processing begins by reading all the data from the saved file. As the count data is read from the file, it is converted into distance using the saved calibration factors (see block 93). The distance data is then placed in a data array so that it can be readily operated on (see block 95). The program can then display the file data, including the file calibration data, the number of points in the file, and the number of points read, and the speed of sound, before proceeding (see block 97).

The program then determines where the valid data ends. In the case of a dropped point, i.e., a sample during which no ultrasound pulse is received, all remaining data is useless to the automatic processing routines. Because the slope of dropped points is very large, dropped points can be found by scanning the distance data to check that the slope between the current point and the previous point is less than some arbitrarily defined value of maximum slope, such as, for example, 100 m/s. If the current point has a slope greater than the predefined maximum slope, then only those distance values up to the current point in the array are saved, establishing the end of valid data (see blocks 99, 101, 103, and 105).

Having established a valid distance data set, the program proceeds to generate the velocity, mean velocity, acceleration, and mean acceleration data arrays. First, however, the data may be filtered (see blocks 107, 109, 111, and 113). If thresholding is selected, the distance data is passed through a 3 pt. median filter to remove minor spikes. The filter performs the initial smoothing of the data. If filtering is selected, the data is bidirectionally filtered using a digital representation of a 4th order Butterworth filter with a cutoff frequency of 6 Hz. As explained more fully below, both the order of the smoothing filter and the cutoff frequency can be changed by the operator. The default, however, is 4th order, 6 Hz cutoff. Bidirectional filtering is used to ensure that the filtering process does not produce a phase lag. As the data is first passed through the filter from first to last point, a phase lag is introduced. By passing this filtered data backwards, i.e., last point to first point, through the filter cancels the phase lag introduced by the first pass.

To eliminate start-up transients associated with the filtering process, a data array three times the size of the original data may be created to place the time inverted data of the distance array into the first and last thirds of this enlarged array. Once bidirectional filtering is completed, only the center third of the enlarged array is put back into the distance array. The output of this process is an array that has been filtered by the equivalent of an 8th order Butterworth filter.

The instantaneous velocity array is next created by differentiating the distance data using a 3 pt. differentiater (see block 115). If thresholding is selected, the instantaneous velocity array is passed through the 3 pt. median filter (see blocks 117 and 119). If filtering is selected, the instantaneous velocity array is then passed through a 4th order bidirectional Butterworth filter with a 6 Hz cutoff frequency (see blocks 121 and 123). Filtering of the instantaneous velocity is performed to remove noise introduced by the differentiation process.

A copy of the instantaneous velocity array is then saved to the mean velocity array (see block 125). The instantaneous velocity is then differentiated to get the instantaneous acceleration (see block 127). If thresholding is selected, the instantaneous acceleration is passed through a 3 pt. median filter (see blocks 129 and 131). If filtering is selected, the instantaneous acceleration is filtered using a 4th order bidirectional Butterworth filter having a 3 Hz cutoff frequency (see blocks 133 and 135). The lower cutoff frequency (than that used for distance and for instantaneous velocity) eliminates features that can upset the automated step time calculation. This filtering also serves to remove noise introduced by the differentiation process.

The mean velocity is next filtered using a bidirectional 4th order Butterworth filter having a 0.6 Hz cutoff frequency (see block 137). The mean velocity is then differentiated to get the mean acceleration (see block 139). The mean acceleration may likewise be filtered to remove noise introduced by the differentiation process.

Now that all the necessary arrays have been produced, the data processing window (i.e., where steady state walking occurs) is determined. This is achieved by analyzing the mean acceleration. The mean acceleration has a very smooth distinct shape during the initiation of gait. It rises from zero to a maximum and then decreases to zero, assuming a constant velocity for steady state walking (in theory). Using this information, steady state walking is defined to commence when the mean acceleration drops 90% from its maximum attained during the initiation of gait. Steady state walking is defined to end when, working backwards from the end of the mean acceleration array, it goes from a positive or negative 10% of the maximum that occurred during gait initiation to below positive or negative 10% of this maximum. This method is used because the initial filtering of the distance data can cause the instantaneous velocity to have a jump at the end of the data set. Working backwards through the mean acceleration array gets to a point where this effect does not skew the data. The start and finish of steady state walking are determined as such at blocks 141, 143, 145, 147 and 149.

Having found the start and finish of steady state walking, a data processing window is established. All the gait parameters are computed by the software automatically using the data that appears within this window. To compute step data values for both legs, the instantaneous acceleration array is scanned for negative to positive crossing points. Linear interpolation between the two points straddling the zero line is used to improve the estimate of the time at which the zero crossing occurred in the data record. This time is saved and the two points in the distance record equivalent in time to the acceleration points are then used to have a linear interpolation performed to find the distance corresponding to the zero crossing time. The zero crossing time and distance is found for every zero crossing in the instantaneous acceleration array. Subtracting the first crossing point from the next crossing point gives the time and length of the first step. Repeating this process and summing each step and making a note of the number of steps until the end of the array enables an overall average step time and length to be computed for the subject.

Repeating the above, except alternating the sum and step counter, such that there is a SumLeg1, SumLeg2 and a Leg1StepCount and a Leg2StepCount enables the step time and step length to be computed for each leg. This whole process is illustrated in blocks 151–81.

Finally, the last value to be computed from the step data is the cadence (step/min) which is given by the following equation (see block 123):

$$\text{Cadence} = (1/\text{Average Step Time Both Legs}) \quad (60)$$

Figure 12:
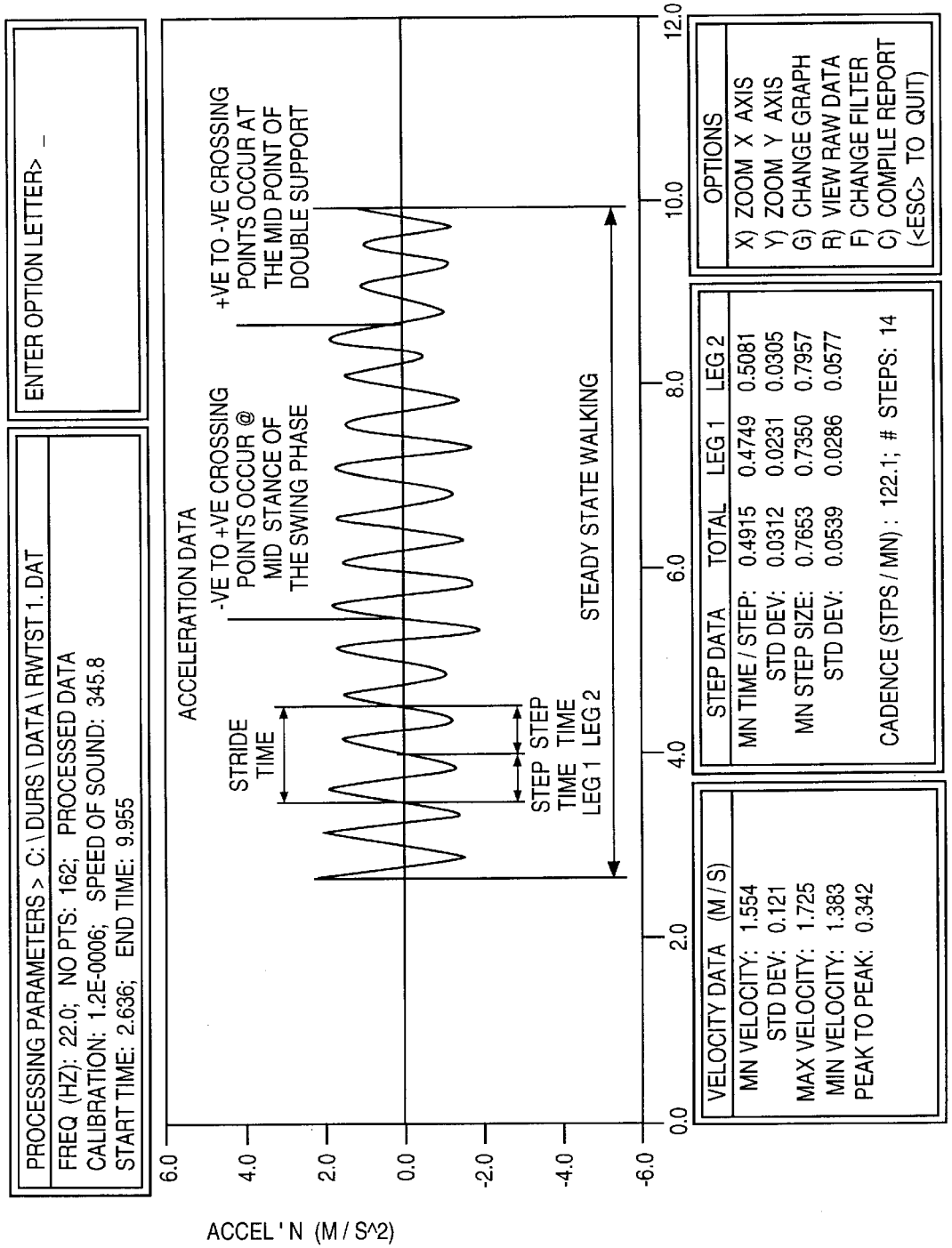
FIG. 12 is one embodiment of a plot of the acceleration data for steady state walking in accordance with the present invention.

FIG. 12 is one embodiment of a plot of the acceleration data for steady state walking. This figure graphically depicts how step time and step length are calculated as discussed above. Also displayed is the calculated cadence.

The next set of gait parameters is computed from the instantaneous velocity and mean velocity arrays. The average walking speed is computed by averaging all of the points of the mean velocity curve that occur within the data processing window (see block 185). The standard deviation of the walking speed is computed from the standard deviation of the instantaneous velocity array within the data processing window (see block 187). The maximum and minimum velocities (see block 189) are computed by the following equations:

$$\text{Max vel.} = \text{Average Walking Speed} + (\sqrt{2})(\text{Std. dev. Walking Speed})$$

$$\text{Min vel.} = \text{Average Walking Speed} - (\sqrt{2})(\text{Std. dev. Walking Speed})$$

The peak to peak fluctuation of the instantaneous velocity (see block 191) is given by the following equation:

$$\text{peak to peak vel. fluctuation} = (2)(\sqrt{2})(\text{Std. dev. Walking Speed})$$

The use of the standard deviations to compute these parameters was done because of the ease of calculation. It is valid for fluctuation about the walking speed that approximates a sinusoid. It may not be a valid assumption for all types of gait pathologies.

Figure 13:
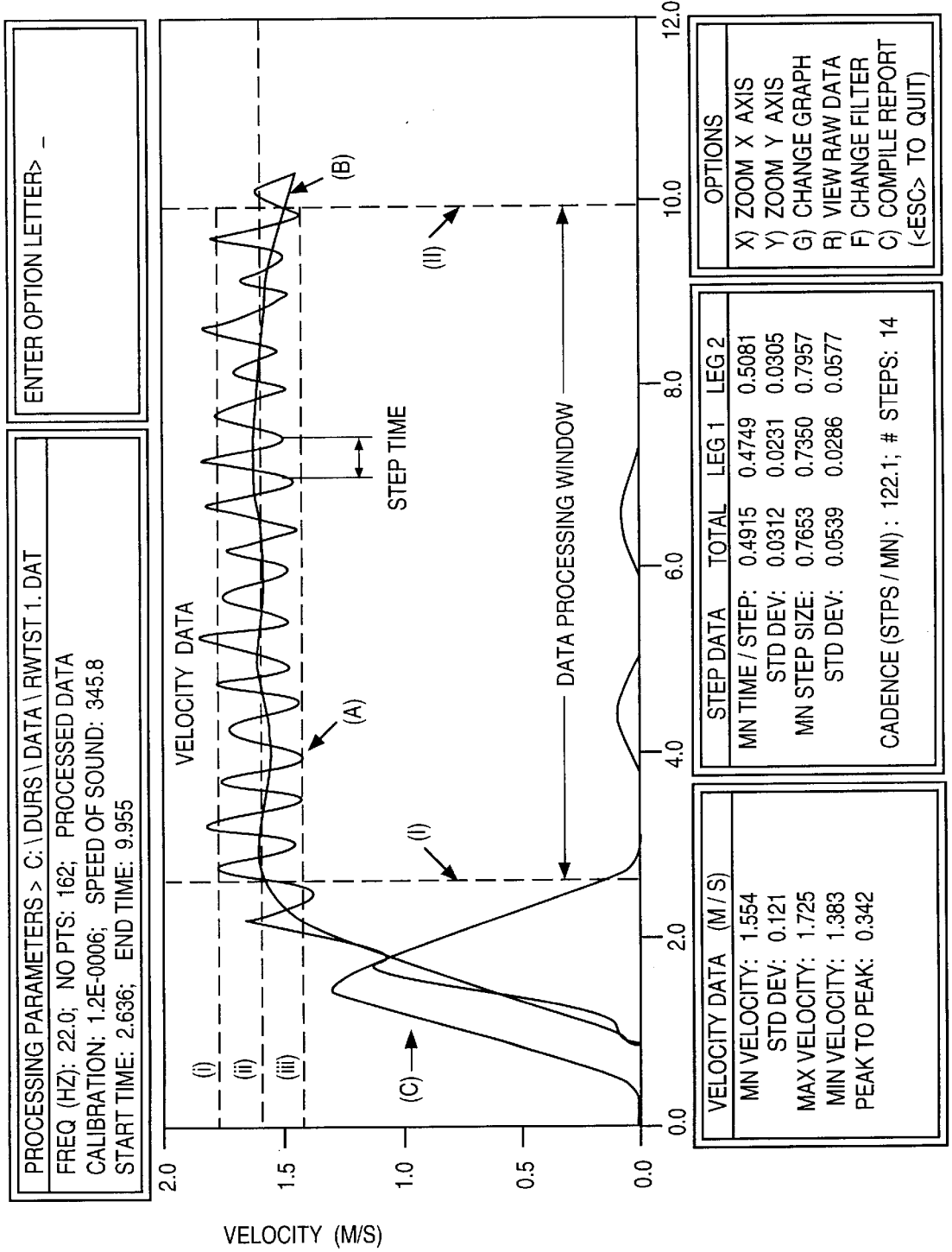
FIG. 13 is one embodiment of a display showing data generated for normal gait in accordance with the present invention.

Now that data arrays and gait parameters have been computed, they, along with the filename, the number of points used in the calculations, the calibration factors, and the speed of sound used to compute the original distance data, are displayed on the screen (see blocks 193, 195, and 197). FIG. 13 is an example of such a display for a normal gait. The curve designated as A is a plot of the instantaneous forward walking velocity. The curves designated as B and C are the mean walking velocity and the mean acceleration, respectively. Dashed vertical line (I) shows were steady state walking begins and dashed vertical line (II) shows where steady state walking ends. Between lines (I) and (II) is the data processing window mentioned above. The horizontal dashed lines (i), (ii), and (iii) represent the maximum instantaneous velocity, the average walking speed, and the minimum instantaneous velocity, respectively.

Figure 14:
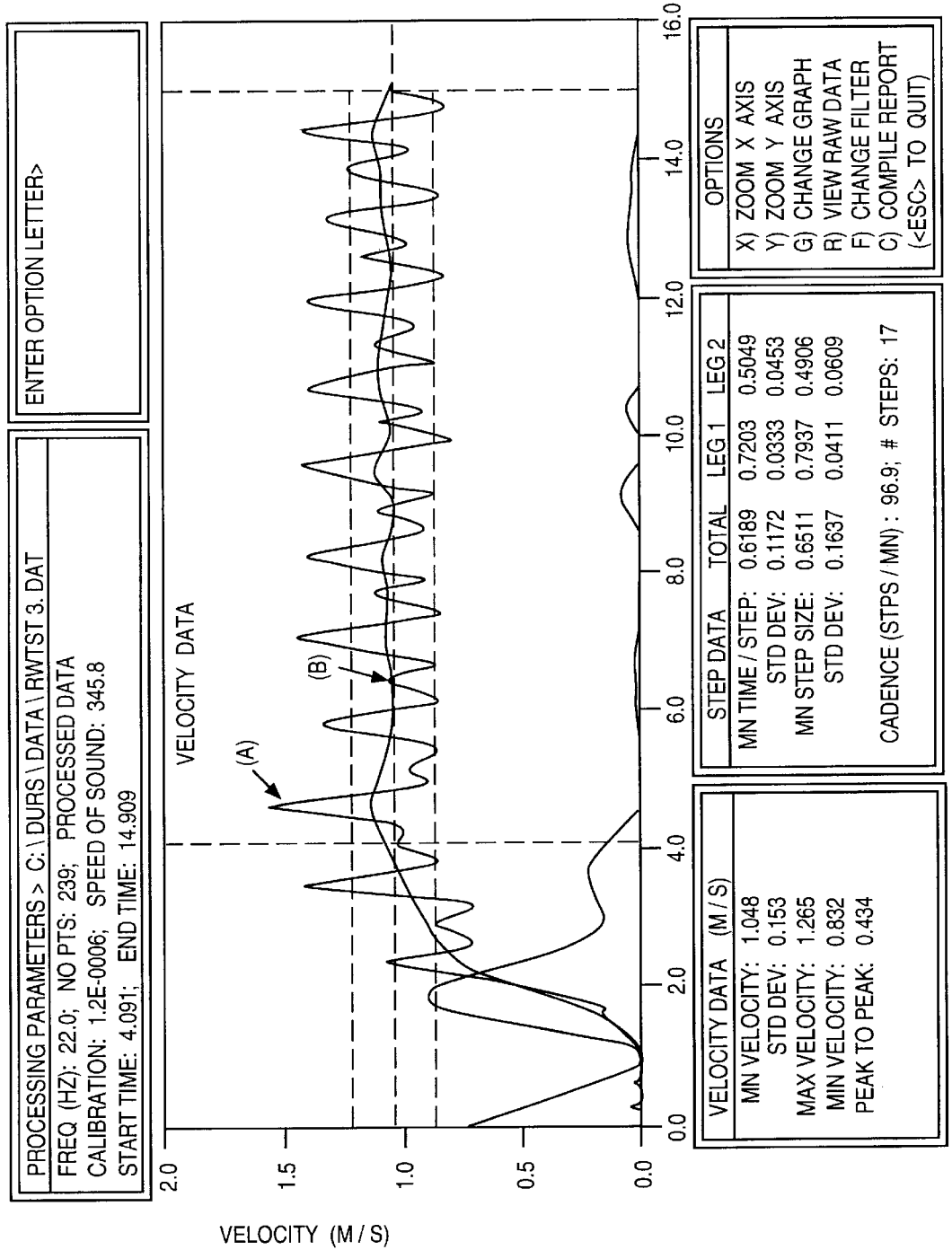
FIG. 14 is one embodiment of a display showing data generated for abnormal gait in accordance with the present invention.

FIG. 14 is a plot similar to FIG. 13, except FIG. 14 represents an abnormal gait. This GVG shows the pattern obtained for a person with a limp.

Referring to the bottom right window in FIGS. 13 and 14, the operator has the choice of selecting from certain options, including changing the ranges of the x or y axes, viewing raw data (i.e., no thresholding or filtering), changing the filter parameters (as mentioned above), changing the display to show instantaneous acceleration or the distance data, generating a report, or returning to the main menu. When the report option is selected, the operator is prompted to enter the subjects name, age, sex, condition, name of operator, date of data acquisition, and any other notes the operator wishes to add. This data, along with the plot data for distance, velocity, mean velocity, acceleration and mean acceleration are all saved to file. These options are shown in FIG. 10 at blocks 199–207.

As mentioned above, when in the main menu, the operator may choose to change the system setup (see block 75). When selected, the setup menu options are displayed (see block 209). These options include quick calibration, full calibration, changing of the COM PORT settings, changing the system sampling rate, or escaping to the main menu (see blocks 211–219).

When quick calibration is selected, the operator is prompted to enter the temperature (see block 223). When full calibration is selected, the operator is also prompted to enter the temperature (see block 225). In addition, however, the operator also measures the counts acquired by the system using two known distances. Using these points, a linear equation is found. The slope of this equation is equivalent to the conversion factor from counts to distance, and the axial intercept is the distance that is added to any conversion to take into account any delays within the system. It should be understood that other calibration methods can be used. For example, a crystal controlled clock that is independent of temperature can be placed in the base unit 3 so that pressing a switch on the unit can place it in a calibrate mode. The computer can then use this reference clock signal to calibrate the interrupt driven software count rate.

Any changes made in the system setup are saved in the configuration upon exit back to the main menu, which can display a timed window with the new settings. Changes are not saved if the operator exits to the main menu using the escape key, which is used throughout the program to exit to the previous program layer.

Many modifications and variations of the present invention are possible in light of the above teachings. For example, while infrared light is used to trigger the ultrasound pulse, other frequencies may be used, such as radio frequencies (e.g., 900 Mhz). In addition, the base unit 3 and the computer terminal 5 may be combined into a single self-contained unit. Thus, it is to be understood that, within the scope of the appended claims, the invention may be practiced otherwise than as described hereinabove.

What is claimed and desired to be secured by Letters Patent is:

1. A portable ranging system comprising:
    circuitry, said circuitry responsive to actuation for initiating a count;
    an infrared emitter, said infrared emitter responsive to said circuitry for emitting high-intensity infrared light to flood a ranging area with infrared light;
    an ultrasound emitter,
    an infrared receiver within the ranging area, said infrared receiver responsive to said infrared light for causing said ultrasound emitter to emit an ultrasound pulse; and
    an ultrasound receiver, said ultrasound receiver responsive to said ultrasound pulse to cause said circuitry to terminate the count, said circuitry using the count to compute the distance between the ultrasound emitter and the ultrasound receiver.

2. The portable ranging system of claim 1 wherein said infrared emitter and said ultrasound receiver are housed in a self-contained unit.

3. The portable ranging system of claim 1 wherein said infrared receiver and said ultrasound emitter are housed in a self-contained battery powered unit.

4. The portable ranging system of claim 1 wherein said infrared emitter is an infrared strobe.

5. The portable ranging system of claim 1 wherein said circuitry includes a computer terminal under software control.

6. The portable ranging system of claim 1 wherein the circuitry performs a count and triggers the infrared emitter during each of a plurality of constant time periods as one of the ultrasound emitter or ultrasound receiver moves relative to the other within the ranging area, and wherein the circuitry uses the counts to compute the distance between the one of the ultrasound emitter or the ultrasound receiver that is moving and the other for each of the plurality of constant time periods.

7. The portable ranging system of claim 6 wherein said circuitry uses the distance computed for each of the plurality of time periods to compute the velocity of the one of the ultrasound emitter or the ultrasound receiver that is moving.

8. The portable ranging system of claim 1 wherein said circuitry includes temperature calibration means for taking into account in the distance computation the effects of temperature on the speed of the ultrasound pulse.

9. The portable ranging system of claim 6 wherein said circuitry includes temperature calibration means for taking into account in the distance computation the effects of temperature on the speed of the ultrasound pulse.

10. The portable ranging system of claim 9 wherein said circuitry uses the distance computed for each of the plurality of time periods to compute the velocity of the one of the ultrasound emitter or the ultrasound receiver that is moving.

11. A portable ranging system comprising:
    circuitry, said circuitry responsive to actuation to initiate a count;
    a base unit having an infrared emitter and an ultrasound receiver, said base unit responsive to the actuation of the circuitry for causing the infrared emitter to emit high-intensity infrared light to flood a ranging area with infrared light;
    a transponder having an infrared receiver and an ultrasound emitter, said transponder responsive to receipt of the infrared light for causing the ultrasound emitter to emit an ultrasound pulse; and
    said base unit responsive to receipt of the ultrasound pulse to cause said circuitry to terminate the count, said circuitry using the count to compute the distance between the transponder and the base unit.

12. The portable ranging system of claim 11 wherein said infrared emitter is an infrared strobe.

13. The portable ranging system of claim 11 wherein said circuitry includes a computer terminal under software control.

14. The portable ranging system of claim 11 wherein said circuitry performs a count and triggers said base unit to cause the infrared emitter to flood the ranging area during each of a plurality of constant time periods as the transponder moves relative to the base unit within the ranging area, and wherein the circuitry uses the counts to compute the distance between the transponder and the base unit for each of the plurality of constant time periods.

15. The portable ranging system of claim 14 wherein said transponder is worn by a subject who is walking.

16. The portable ranging system of claim 15 wherein the circuitry computes a plurality of gait parameters for the walking subject.

17. The portable ranging system of claim 16 wherein the circuitry includes a computer terminal under software control having a display, and wherein the computer terminal displays the plurality of gait parameters on the display.

18. The portable ranging system of claim 17 wherein the plurality of gait parameters includes at least two of mean walking velocity, mean acceleration, instantaneous forward walking velocity, maximum walking velocity, minimum walking velocity, step length, step time, cadence, average walking velocity, maximum instantaneous velocity, peak to peak velocity variation, time to achieve steady state walking and minimum instantaneous velocity.

19. In a portable ranging system having circuitry, a base unit, and a transponder, the method of computing the velocity of the transponder as it moves relative to the base unit within a ranging area, the method comprising the steps of:
    (a) counting by the circuitry in response to an actuation of the circuitry,
    (b) triggering by the circuitry the base unit in response to the actuation of said circuitry;
    (c) flooding by the base unit the ranging area with infrared light in response to said triggering;
    (d) receiving by the transponder the infrared light;
    (e) emitting by the transponder an ultrasound pulse in response to said step of receiving by the transponder of the infrared light;
    (f) receiving by the base unit the ultrasound pulse;
    (g) signalling by the base unit said circuitry in response to said step of receiving by the base unit the ultrasound pulse;
    (h) terminating by said circuitry said counting in response to said step of signalling;
    (i) repeating steps (a) through (h) for each of a plurality of constant time periods;
    (j) computing using count data from said counting the distance of the transponder from the base unit for each of the plurality of constant time periods; and
    (k) differentiating the distance data computed in step (j) to obtain the velocity.

20. The method of claim 19 wherein the circuitry includes a computer terminal having a display, the method further comprising the step of:
    (1) displaying by the circuitry the velocity data on the display.

21. A portable ranging system comprising:
    circuitry, said circuitry responsive to actuation for initiating a count;
    an infrared emitter, said infrared emitter responsive to said circuitry for emitting high-intensity infrared light to flood a ranging area with infrared light;
    an ultrasound emitter;
    an infrared receiver,
        said infrared receiver responsive to infrared light for causing said ultrasound emitter to emit an ultrasound pulse;
    an ultrasound receiver, said ultrasound receiver responsive to a signal for causing said circuitry to terminate the count, said circuitry using the count to compute the distance between the ultrasound emitter and the ultrasound receiver; and
    means for ensuring that the signal is the ultrasound pulse.

22. The portable ranging system of claim 21 wherein said infrared emitter, said ultrasound receiver, and said means are housed in a selfcontained unit.

23. The portable ranging system of claim 21 wherein said infrared receiver and said ultrasound emitter are housed in a self-contained battery powered unit.

24. The portable ranging system of claim 21 wherein the infrared emitter floods the ranging area with infrared light.

25. The portable ranging system of claim 24 wherein the infrared emitter is an infrared strobe.

26. The portable ranging system of claim 21 wherein said circuitry includes a computer terminal under software control.

27. The portable ranging system of claim 21 wherein the circuitry performs a count and triggers the infrared emitter during each of a plurality of constant time periods as one of the ultrasound emitter or ultrasound receiver moves relative to the other within the ranging area, and wherein the circuitry uses the counts to compute the distance between the one of the ultrasound emitter or the ultrasound receiver that is moving and the other for each of the plurality of constant time periods.

28. The portable ranging system of claim 27 wherein said circuitry uses the distance computed for each of the plurality of time periods to compute the velocity of the one of the ultrasound emitter or the ultrasound receiver that is moving.

29. The portable ranging system of claim 21 wherein said circuitry includes temperature calibration means for taking into account in the distance computation the effects of temperature on the speed of the ultrasound pulse.

30. The portable ranging system of claim 27 wherein said circuitry includes temperature calibration means for taking into account in the distance computation the effects of temperature on the speed of the ultrasound pulse.

31. The portable ranging system of claim 30 wherein said circuitry uses the distance computed for each of the plurality of time periods to compute the velocity of the one of the ultrasound emitter or the ultrasound receiver that is moving.

32. A portable ranging system comprising:

circuitry, said circuitry responsive to actuation for initiating a count;

a base unit having an infrared emitter and an ultrasound receiver, said base unit causing the infrared emitter to emit high-intensity infrared light for flooding a ranging area with infrared light;

a transponder having an infrared receiver and an ultrasound emitter, said transponder responsive to receipt of the infrared light for causing the ultrasound emitter to emit an ultrasound pulse;

means responsive to the circuitry for preventing noise received and/or present in the system from falsely triggering the receipt of an ultrasound pulse, and for causing said circuitry to terminate the count upon receipt of the ultrasound pulse; and said circuitry using the count to compute the distance between the transponder and the base unit.

33. A portable ranging system comprising:

processing circuitry;

control circuitry, said control circuitry causing the initiation of a count by the processing circuitry;

an infrared emitter, said infrared emitter responsive to said control circuitry for flooding a ranging area with infrared light, an infrared receiver for receiving the infrared light;

an ultrasound emitter for emitting an ultrasound pulse within the ranging area;

an ultrasound receiver, said ultrasound receiver responsive to said ultrasound pulse to cause the processing circuitry to terminate the count, said processing circuitry performing a count and the control circuitry triggering the infrared emitter during each of a plurality of constant time periods as one of the ultrasound emitter or ultrasound receiver moves relative to the other within the ranging area; and said processing circuitry using the count to compute the distance between the one of the ultrasound emitter and the ultrasound receiver that is moving and the other for each of the plurality of constant time periods, said processing circuitry using the distance computed for each of the plurality of time periods to compute the velocity of the one of the ultrasound emitter or the ultrasound receiver that is moving.

34. The portable ranging system of claim 33 wherein the infrared emitter is an infrared strobe.

35. The portable ranging system of claim 32 wherein said circuitry performs a count and triggers said base unit to cause the infrared emitter to emit infrared light within the ranging area during each of a plurality of constant time periods as the transponder moves relative to the base unit within the ranging area, and wherein the circuitry uses the counts to compute the distance between the transponder and the base unit for each of the plurality of constant time periods.

36. The portable ranging system of claim 35 wherein said transponder is worn by a subject who is walking.

37. The portable ranging system of claim 36 wherein the circuitry computes a plurality of gait parameters for the walking subject.

38. The portable ranging system of claim 37 wherein the circuitry includes a computer terminal under software control having a display, and wherein the computer terminal displays the plurality of gait parameters on the display.

39. The portable ranging system of claim 38 wherein the plurality of gait parameters includes at least two of mean walking velocity, mean acceleration, instantaneous forward walking velocity, maximum walking velocity, minimum walking velocity, step length, step time, cadence, average walking, velocity, maximum instantaneous velocity, peak to peak velocity vriation, time to achieve steady state walking and minimum instantaneous velocity.

40. In a portable ranging system having circuitry, a base unit, and a transponder, the method of computing the velocity of the transponder as it moves relative to the base unit within a ranging area, the method comprising the steps of:

(a) counting by the circuitry in response to an actuation of the circuitry, (b) triggering by the circuitry the base unit in response to the actuation of the circuitry;

(c) emitting by the base unit within the ranging area infrared light in response to said step of triggering;

(d) receiving by the transponder the infrared light;

(e) emitting by the transponder an ultrasound pulse in response to said step of receiving by the transponder the infrared light;

(f) receiving by the base unit of signals;

(g) determining by the base unit that one of the signals received is the ultrasound pulse;

(h) signalling by the base unit said circuitry in response to said step of determining;

(i) terminating by said circuitry said counting in response to said step of signalling;

(j) repeating steps (a) through (i) for each of a plurality of constant time periods;

(k) computing by the circuitry using count data the distance of the transponder from the base unit for each of the plurality of constant time periods; and (l) differentiating the distance data computed in step (k) to obtain the velocity.

41. The method of claim 40 wherein the circuitry includes a computer terminal having a display, the method further comprising the step of:

(m) displaying by the circuitry the velocity data on the display.

42. A portable ranging system comprising:

processing circuitry;

control circuitry, said control circuitry causing the initiation of a count by the processing circuitry;

an infrared emitter, said infrared emitter responsive to said control circuitry for emitting high-intensity infrared light to flood a ranging area with infrared light, an infrared receiver for receiving the infrared light;

an ultrasound emitter for emitting an ultrasound pulse within the ranging area;

an ultrasound receiver, said ultrasound receiver responsive to said ultrasound pulse to cause the processing circuitry to terminate the count; and said processing circuitry using the count to compute the distance between the ultrasound emitter and the ultrasound receiver.

43. The portable ranging system of claim 42 wherein the processing circuitry performs a count and the control circuitry triggers the infrared emitter during each of a plurality of constant time periods as one of the ultrasound emitter or ultrasound receiver moves relative to the other within the ranging area, and wherein the processing circuitry uses the counts to compute the distance between the one of the ultrasound emitter or the ultrasound receiver that is moving and the other for each of the plurality of constant time periods.

44. The portable ranging system of claim 43 wherein said processing circuitry uses the distance computed for each of the plurality of time periods to compute the velocity of the one of the ultrasound emitter or the ultrasound receiver that is moving.

45. A portable ranging system comprising:

circuitry, said circuitry responsive to actuation for initiating a count;

an infrared emitter, said infrared emitter responsive to said circuitry for emitting infrared light in a ranging area;

an ultrasound emitter;

an infrared receiver, said infrared receiver responsive to infrared light for causing said ultrasound emitter to emit an ultrasound pulse;

an ultrasound receiver, said ultrasound receiver responsive to a signal for causing said circuitry to terminate the count, said circuitry performing a count and triggering the infrared emitter during each of a plurality of constant time periods as one of the ultrasound emitter or ultrasound receiver moves relative to the other within the ranging area, said circuitry using the count to compute the distance between the one of the ultrasound emitter and the ultrasound receiver that is moving and the other for each of the plurality of constant time periods, said circuitry using the distance computed for each of the plurality of time periods to compute the velocity of the one of the ultrasound emitter or the ultrasound receiver that is moving; and means for ensuring that the signal is the ultrasound pulse.

46. The portable ranging system of claim 45 wherein said circuitry includes temperature calibration means for taking into account in the distance computations the effects of temperature on the speed of the ultrasound pulse.

47. The portable ranging system of claim 46 wherein the infrared emitter floods the ranging area with infrared light.

48. The portable ranging system of claim 47 wherein the infrared emitter is an infrared strobe.

49. A portable ranging system comprising:

circuitry, said circuitry responsive to actuation for initiating a count;

a base unit having an infrared emitter and an ultrasound receiver, said base unit causing the infrared emitter to emit infrared light within a ranging area;

a transponder worn by a subject who is walking, said transponder having an infrared receiver and an ultrasound emitter, said transponder responsive to receipt of the infrared light for causing the ultrasound emitter to emit an ultrasound pulse; and means for preventing noise received and/or present in the system from falsely triggering the receipt of an ultrasound pulse, and for causing said circuitry to terminate the count upon receipt of the ultrasound pulse, said circuitry performing a count and triggering said base unit to cause the infrared emitter to emit infrared light within the ranging area during each of a plurality of constant time periods as the transponder moves relative to the base unit within the ranging area;

said circuitry using the count to compute the distance between the transponder and the base unit for each of the plurality of constant time periods, and said circuitry computing a plurality of gait parameters for the walking subject.

50. The portable ranging system of claim 49 wherein the circuitry includes a computer terminal under software control having a display, and wherein the computer terminal displays the plurality of gait parameters on the display.

51. The portable ranging system of claim 50 wherein the plurality of gait parameters includes at least two of mean walking velocity, mean acceleration, instantaneous forward walking velocity, maximum walking velocity, minimum walking velocity, step length, step time, cadence, average walking velocity, maximum instantaneous velocity, peak to peak velocity variation, time to achieve steady state walking and minimum instantaneous velocity.

52. In a portable ranging system having control circuitry, processing circuitry, thresholding circuitry, an ultrasound emitter, and an ultrasound receiver, the method of computing the velocity of one of the ultrasound emitter or ultrasound receiver as the one moves relative to the other, said method comprising the steps of:

(a) causing by said control circuitry the triggering of the processing circuitry and the ultrasound emitter;

(b) counting by the processing circuitry in response to said triggering;

(c) emitting by the ultrasound emitter an ultrasound pulse in response to said triggering;

(d) receiving by the ultrasound receiver signals;

(e) comparing by the thresholding circuitry the signals received by the ultrasound emitter to a time varying adaptive threshold;

(f) signalling by the thresholding circuitry the processing circuitry when a signal received is greater than the time varying adaptive threshold;

(g) terminating by the processing circuitry said counting in response to said step of signalling; and (h) repeating steps (a) through (g) for each of a plurality of constant time periods;

(i) calculating using count data from said counting the distance of the ultrasound emitter from the ultrasound receiver for each of the plurality of constant time periods;

(j) differentiating the distance data calculated in step (i) to obtain velocity.

53. The method of claim 52 wherein the processing circuitry includes a computer terminal and a display, said method further comprising the step of:

(k) displaying by the control circuitry the velocity data on the display.

54. A portable ranging system comprising:

processing circuitry;

an ultrasound emitter;

control circuitry, said control circuitry causing the initiation of a count by the processing circuitry and for causing the ultrasound emitter to emit an ultrasound pulse;

an ultrasound receiver;

means for analyzing signals received at the ultrasound receiver for determining that the ultrasound pulse has been received, and for causing said processing circuitry to terminate the count upon receipt of the ultrasound pulse, said processing circuitry performing a count and the control circuitry causing the ultrasound emitter to emit an ultrasound pulse during each of a plurality of constant time periods as one of the ultrasound emitter or ultrasound receiver moves relative to the other within the ranging area, and said processing circuitry using the count to compute the distance between the one of the ultrasound emitter and the ultrasound receiver that is moving and the other for each of the plurality of constant time periods, said processing circuitry using the distance computed for each of the plurality of time periods to compute the velocity of the one of the ultrasound emitter or the ultrasound receiver that is moving.

55. A portable ranging system comprising:

circuitry, said circuitry responsive to actuation for initiating a count;

an infrared emitter, said infrared emitter responsive to said circuitry for flooding a ranging area with infrared light;

an ultrasound emitter, an infrared receiver within the ranging area, said infrared receiver responsive to said infrared light for causing said ultrasound emitter to emit an ultrasound pulse; and an ultrasound receiver, said ultrasound receiver responsive to said ultrasound pulse to cause said circuitry to terminate the count, said circuitry performing a count and triggering the infrared emitter during each of a plurality of constant time periods as one of the ultrasound emitter or ultrasound receiver moves relative to the other within the ranging area, said circuitry using the count to compute the distance between the one of the ultrasound emitter and the ultrasound receiver that is moving and the other for each of the plurality of constant time periods, said circuitry using the distance computed for each of the plurality of time periods to compute the velocity of the one of the ultrasound emitter or the ultrasound receiver that is moving.

56. The portable ranging system of claim 55 wherein said circuitry includes temperature calibration means for taking into account in the distance computations the effects of temperature on the speed of the ultrasound pulse.

57. A portable ranging system comprising:

circuitry, said circuitry responsive to actuation to initiate a count;

a base unit having an infrared emitter and an ultrasound receiver, said base unit responsive to the actuation of the circuitry for causing the infrared emitter to flood a ranging area with infrared light;

a transponder worn by subject who is walking, said transponder having an infrared receiver and an ultrasound emitter, said transponder responsive to receipt of the infrared light for causing the ultrasound emitter to emit an ultrasound pulse; and said base unit responsive to receipt of the ultrasound pulse to cause said circuitry to terminate the count, said circuitry performing a count and triggering said base unit to cause the infrared emitter to flood the ranging area during each of a plurality of constant time periods as the transponder moves relative to the base unit within the ranging area, said circuitry using the count to compute the distance between the transponder and the base unit for each of the plurality of constant time periods, and said circuitry computing a plurality of gait parameters for the walking subject.

58. The portable ranging system of claim 57 wherein the circuitry includes a computer terminal under software control having a display, and wherein the computer terminal displays the plurality of gait parameters on the display.

59. The portable ranging system of claim 58 wherein the plurality of gait parameters includes at least two of mean walking velocity, mean acceleration, instantaneous forward walking velocity, maximum walking velocity, minimum walking velocity, step length, step time, cadence, average walking velocity, maximum instantaneous velocity, peak to peak velocity variation, time to achieve steady state walking and minimum instantaneous velocity.

60. A portable ranging system comprising:

an infrared emitter for emitting an infrared pulse for each of a plurality of time periods;

an ultrasound emitter;

an infrared receiver, said infrared receiver responsive to the infrared pulse received for causing the ultrasound emitter to emit an ultrasound pulse for each of the plurality of time periods;

an ultrasound receiver for receiving the ultrasound pulse for each of the plurality of time periods;

circuitry for determining an elapsed time from emission of the infrared pulse to receipt of the ultrasound pulse for each of the plurality of time periods as one of the ultrasound emitter or ultrasound receiver moves relative to the other; and said circuitry using the elapsed time for each of the plurality of time periods to calculate at least one of a plurality of parameters for the one of the ultrasound emitter or ultrasound receiver that moves, said plurality of parameters comprised of mean velocity, mean acceleration, instantaneous forward velocity, maximum velocity, minimum velocity, and peak to peak velocity variation.

61. The portable ranging system of claim 60 wherein the circuitry includes a computer terminal under software control having a display, and wherein the computer terminal displays the at least one of the plurality of parameters on the display.

62. The portable ranging system of claim 61 wherein the at least one of the plurality of parameters is displayed in a graphical format.

63. The portable ranging system of claim 61 wherein the at least one of the plurality of parameters is displayed in real time as the one of the ultrasound emitter or ultrasound receiver moves.

64. The portable ranging system of claim 62 wherein the at lest one of the plurality of parameters is displayed in real time as the one of the ultrasound emitter or ultrasound receiver moves.

65. A portable ranging system comprising:

a base unit having an infrared emitter and an ultrasound receiver, said infrared emitter for emitting an infrared pulse for each of a plurality of time periods;

a transponder having an infrared receiver and an ultrasound emitter, said infrared receiver responsive to the infrared pulse for causing the ultrasound emitter to emit an ultrasound pulse for each of the plurality of time periods, said ultrasound receiver for receiving the ultrasound pulse for each of the plurality of time periods;

circuitry for determining an elapsed time from emission of the ultrasound pulse to receipt of the ultrasound pulse for each of the plurality of time periods; and said circuitry using the elapsed time for each of the plurality of time periods to calculate at least one of a plurality of parameters for the transponder as it moves, said plurality of parameters comprised of mean velocity, mean acceleration, instantaneous forward velocity, maximum velocity, minimum velocity, and peak to peak velocity variation.

66. The portable ranging system of claim 65 wherein the circuitry includes a computer terminal under software control having a display, and wherein the computer terminal displays the at least one of the plurality of parameters on the display.

67. The portable ranging system of claim 66 wherein the transponder is worn by a walking subject and the at least one of the plurality of parameters comprises at least one gait parameter for the walking subject.

68. The portable ranging system of claim 66 wherein the at least one of the plurality of parameters is displayed in a graphical format.

69. The portable ranging system of claim 66 wherein the at least one of the plurality of parameters is displayed in real time as the transponder moves.

70. The portable ranging system of claim 68 wherein the at least one of the plurality of parameters is displayed in real time as the transponder moves.

71. The portable ranging system of claim 67 wherein the at least one gait parameter is displayed in a graphical format.

72. The portable ranging system of claim 67 wherein the at least one gait parameter is displayed in real time as the subject walks.

73. The portable ranging system of claim 71 wherein the at least one gait parameter is displayed in real time as the subject walks.

74. A portable ranging system comprising:
an ultrasound emitter for emitting an ultrasound pulse for each of a plurality of time periods;
an ultrasound receiver for receiving the ultrasound pulse for each of the plurality of time periods;
circuitry for determining an elapsed time from emission of the ultrasound pulse to receipt of the ultrasound pulse for each of the plurality of time periods as one of the ultrasound emitter or ultrasound receiver moves relative to the other; and
said circuitry using the elapsed time for each of the plurality of time periods to calculate at least one of a plurality of parameters for the one of the ultrasound emitter or ultrasound receiver that moves, said plurality of parameters comprised of mean velocity, mean acceleration, instantaneous forward velocity, maximum velocity, minimum velocity, and peak to peak velocity variation.

75. The portable ranging system of claim 74 wherein the circuitry includes a computer terminal under software control having a display, and wherein the computer terminal displays the at least one of the plurality of parameters on the display.

76. The portable ranging system of claim 75 wherein the at least one of the plurality of parameters is displayed in a graphical format.

77. The portable ranging system of claim 75 wherein the at least one of the plurality of parameters is displayed in real time as the one of the ultrasound emitter or ultrasound receiver moves.

78. The portable ranging system of claim 76 wherein the at least one of the plurality of parameters is displayed in real time as the one of the ultrasound emitter or ultrasound receiver moves.

79. The portable ranging system of claim 74 wherein the ultrasound emitter is worn by a walking subject and the at least one of the plurality of parameters comprises at least one gait parameter for the walking subject.

80. The portable ranging system of claim 75 wherein the ultrasound emitter is worn by a walking subject and the at least one of the plurality of parameters comprises at least one gait parameter for the walking subject.

81. The portable ranging system of claim 80 wherein the at least one gait parameter is displayed in a graphical format.

82. The portable ranging system of claim 80 wherein the at least one gait parameter is displayed in real time as the subject walks.

83. The portable ranging system of claim 81 wherein the at least one gait parameter is displayed in real time as the subject walks.

84. A portable ranging system comprising;
processing circuitry;
an ultrasound emitter,
control circuitry, said control circuitry responsive to actuation for causing the initiation of a count by the processing circuitry and for causing the ultrasound emitter to emit an ultrasound pulse;
an ultrasound receiver;
circuitry for comparing signals received at the ultrasound receiver to a time varying adaptive threshold and for causing said processing circuitry to terminate the count when the signal received is greater than the threshold, said processing circuitry performing a count and said control circuitry causing the ultrasound emitter to emit an ultrasound pulse during each of a plurality of constant time periods as one of the ultrasound emitter or ultrasound receiver moves relative to the other within the ranging area; and
said processing circuitry using the count to compute the distance between the one of the ultrasound emitter and the ultrasound receiver that is moving for each of the plurality of constant time periods, said processing circuitry using the distance computed for each of the plurality of time periods to compute the velocity of the one of the ultrasound emitter or the ultrasound receiver that is moving.

* * * * *